US006465625B1

(12) United States Patent
Dordick et al.

(10) Patent No.: US 6,465,625 B1
(45) Date of Patent: *Oct. 15, 2002

(54) TAXOL DERIVATIVES

(75) Inventors: Jonathan S. Dordick, Iowa City, IA (US); Douglas S. Clark, Oakland, CA (US); Peter C. Michels, Iowa City, IA (US); Yuri L. Khmelnitsky, Iowa City, IA (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/596,545

(22) Filed: Jun. 19, 2000

Related U.S. Application Data

(63) Continuation of application No. 09/091,833, filed as application No. PCT/US96/14573 on Sep. 11, 1996, now Pat. No. 6,136,961.
(60) Provisional application No. 60/003,661, filed on Sep. 11, 1995.

(51) Int. Cl.⁷ ..................... C07H 17/08; C07D 305/00; C07D 311/00
(52) U.S. Cl. ..................... 536/17.9; 536/17.2; 536/17.5; 536/17.6; 536/18.1; 549/385; 549/387; 549/388; 549/510; 549/511
(58) Field of Search ..................... 536/7.2, 7.4, 17.2, 536/17.5, 17.9, 18.1; 549/385, 387, 388, 510, 511

(56) References Cited

U.S. PATENT DOCUMENTS

| 2,653,899 A |   | 9/1953 | Bunch et al. |
| 4,826,820 A |   | 5/1989 | Brain |
| 5,141,926 A |   | 8/1992 | Weber et al. |
| 5,906,990 A |   | 5/1999 | Bouchard et al. |
| 6,136,961 A | * | 10/2000 | Dordick et al. ............... 536/7.5 |

FOREIGN PATENT DOCUMENTS

WO    WO 89/08453    9/1989

OTHER PUBLICATIONS

Astorga, et al. "Enzymatic hydrazinolysis of diesters and synthesis of N–aminosuccinimide derivatives," *Synthesis—Stuttgart* 3: 287–289 (1993).
Athawale, et al. "Enzymatic synthesis of polyesters by lipase catalyzed polytransesterification," *Biotechnology Letters* 16 (2): 149–154, (1994).
Baldessari, et al. "Regioselective acylation of 3–mercaptopropane-1,2–diol by lipase–catalyzed transesterification," *Journal of Chemical Research—S* 382–383, (1993).
Bergbreiter, et al. "Asymmetric synthesis of organometallic reagents using enzymatic methods," *Applied Biochemistry and Biotechnology* 32 (1–3): 55–72 (1992).

Bianchi, et al . "Enzymatic preparation of optically active fungicide intermediates in aqueous and in organic media," *Pure and Applied Chemistry* 64 (8): 1073–1078 (1992).
Bianchi, et al. "Enzymatic preparation of optically active fungicide intermediates in aqueous and in organic media," *Indian Journal of Chemistry Section B—Organic Chemistry Including Medicinal Chemistry* 32 (1): 176–180 (1993).
Bunnage, et al. "Asymmetric Synthesis of the Taxol and Taxotére C–13 Side Chains" *J. Chem. Soc., Perkin Trans.* 1, 17:2385–2391. (1994).
Cabezas, et al. "Organic reactions catalyzed by modified enzymes. 1. Alteration of the substrate specificity of a–chymotrypsin by the modification process," *Journal of Molecular Catalysis* 71(2) 261–278, (1992).
Carretero, et al. "Lipase–catalyzed kinetic resolution of gamma hydroxy phenyl sulfones," *Journal of Organic Chemistry* 57 (14): 3867–3873 (1992).
Chen, et al. "General aspects and optimization of enantioselective biocatalysis in organic solvents: The use of lipases," *Angew. Chem*(Int. Ed. Engl. 28, 6:695–707 (1989).
Chmurny, et al. "1H– and 13C–nmr assignments for taxol, 7–epi–taxol, and cephalomannine," *J. Nat. Prod.* 55: 414–423 (1992).
Cruces, et al. "Enzymatic preparation of acylated sucrose," Ann. New York Acad. Sci. (Enzyme Eng. XI, D.S. Clark, D.A. Estell, eds) 672: 436–443 (1992).
Csuk, et al. "Baker's yeast mediated transformations in organic chemistry," *Chem. Rev.* 91 (1): 49–97 (1991).
De Goede, et al. "Selective lipase–catalyzed 6–O–acylation of alkyl alpha–D–glucopyranosides using functionalized ethyl esters," *Recueil des Travaux Chimiques des Pays Bas—Journal of the Royal Netherlands Chemical Society* 112(11): 567–572 (1993).
Deutsch, et al. "Synthesis of congeners and prodrugs. 3. Water–soluble prodrugs of taxol with potent antitumor activity," *J Med Chem.* 32 (4): 788–92 (1989).
Dondoni, et al. "Synthesis of Taxol and Taxotere Side Chains by 2–(Trimrthylsilyl)thiazole Based Homologation of L–Phenylglycine," *Synthesis—Stuttgart* 2: 181–186 (1995).
Fabre, et al., "Regiospecific enzymic acylation of butlyl a–D–glucopyranoside," *Carbohydrate Research* 243 (2): 407–411 (1993).
Ferjancic, et al., "Unusual specificity of Polyethylene glycol modified themolysin in peptide synthesis catalyzed in organic solvents," *Biotechnology Letters* 10 (2):101–106 (1988).
Fitzpatrick, et al. "How can the solvent affect enzyme enantioselectivity?" *JACS* 113 (8): 3166–3171 (1991).
Forastiere, et al. "Use of paclitaxel (Taxol) in squamous cell carcinoma of the head and neck," *Semin Oncol.* (4 Suppl 3):56–60 (1993).

(List continued on next page.)

*Primary Examiner*—Elli Peselev
(74) *Attorney, Agent, or Firm*—Nixon Peabody LLP

(57) ABSTRACT

Highly specific biocatalytic reactions have been used to create a population of taxol derivatives.

18 Claims, 7 Drawing Sheets

OTHER PUBLICATIONS

Frykman, et al. "S–Ethyl thiooctanoate as acyl donor in lipase catalyzed resolution of secondary alcohols," *Tetrahedron Letters* 34(8): 1367–1370 (1993).

Fukui, et al. "Enzymatic preparation of optically active silylmethanol derivatives having a stereogenic silicon atom by hydrolase–catalyzed enantioselctive esterification," *Tetrahedron: Asymmetry* 5 (1): 73–82 (1994).

Georg, et al. "Synthesis of biologically active taxol analogues with modified phenylisoserine side chains," *J Med Chem* 35 (22):4230–7 (1992).

Gololobov, et al. "Organic solvent changes the chymotrypsin specificity with respect to nucleophiles," *FEBS Letters* 307 (3):309–312 (1992).

Greenwald et al. "Highly Water Soluble Taxol Derivatives: 2'Polyethyleneglycol Esters as potential Prodrugs," *Bioorg. Med. Chem. Lett* 4: (20):2465–2470 (1994).

Greenwald et al. "Drug delivery systems: water soluble taxol 2'–poly(ethylene glycol) ester prodrugs–design and in vivo effectiveness," *J Med Chem.* 39(2):424–31 (1996).

Greenwald et al. "Highly Water Soluble Taxol Derivatives: 7–Polyethylene Glycol Carbamates and Carbonates," *Org. Chem* 60:331–336 (1995).

Guenard, et al. "Taxol and Taxotere: Discovery, Chemistry, and Structure–Activity Relationships," *Acc. Chem. Res.* 26:160–167 (1993).

Hanson, et al. "Site–specific enzymatic hydrolysis of taxanes at C–10 and C–13," *J Biol Chem.* 269 (35): 22145–9 (1994).

Herradon, "Biocatalytic synthesis of chiral polyoxgenated compounds: effect of the solvent on the enantioselectivity of lipase catalyzed transesterifications in organic solvents," *Synlett* 2 :108–110 (1993).

Hertmanni, et al. Orientation of enzyme catalysis and specificity by water–soluble additives. *Ann. New York Acad. Sci.* (Enzyme Eng. XI, D.S. Clark, D.A. Estell, eds) 672:329–335 (1992).

Holton, et al. "First Total Synthesis of Taxol. 1. Functionlization of the B Ring," *JACS* 116: 1597–1598 (1994).

Holton, et al. "First Total Synthesis of Taxol. 2. Completion of the C and D Rings,"*JACS,* 116: 1599–1600 (1994).

Huang, et al. "New taxanes from *Taxus brevifolia*, 2" *J Nat Prod.* 49 (4):665–9 (1986).

Hult, et al. Enantioselectivity of some lipases—control and prediction. *Pure and Applied Chemistry* 64 (8): 1129–1134 (1992).

Hyun, et al. "Enhancement effect of water activity on enzymatic synthesis of cephalexin," *Biotechnology and Bioengineering* 42 (7): 800–806 (1993).

Ikeda, et al. "Lipase–catalyzed acylation of sugars solubilized in hydrophobic solvents by complexation," *Biotechnology and Bioengineering* 42 (6): 788–791 (1993).

Izumi, et al. "Enzymatic kinetic resolution of[4] (1,2) ferrocenophane derivatives," *Bulletin of the Chemical Society of Japan* 65 (10): 2784–2788 (1992).

Janssen, et al. "Lipase–catalyzed synthesis of oleic acid esters of polyethylene glycol 400," *Biotechnology Letters* 16 (2): 163–168 (1994).

Johnson, et al. "Applications of enzymes in the synthesis of bioactive polyols," *Indian Journal of Chemistry Section B—Organic Chemistry Including Medicinal Chemistry* 32 (1): 140–144 (1993).

Johnson, et al. "Enzymatic asymmetrization in organic media—synthesis of unnatural glucose from cycloheptatriene," *JACS* 114(24): 9414–9418 (1992).

Jones, et al. "Enzymes in organic synthesis," *Tetrahedron* 42 (13): 3351–3405 (1986).

Kanerva, et al. "Enzymatic acylation in the resolution of methyl threo–2–hydroxy–3–(4–methoxyphenyl)–3–(2–X–phenylthio) propionates in organic solvents," *Journal of the Chemical Society—Perkins Transactions I* 20: 2407–2410 (1993).

Kanerva, et al. "Lipase catalysis in the resolution of racemic intermediates of diltiazem synthesis in organic solvents," *Journal of the Chemical Society—Perkin Transactions I* 13: 1385–1389 (1993).

Khmelnitsky, et al. "Engineering biocatalytic systems in organic media with low water content," *Enzyme Microb. Technol.* 10: 710 (1988).

Khmelnitsky, et al. "Salts dramatically enhance activity of enzymes suspended in organic solvents," *JACS* 116: 2647–2648 (1994).

Kingston, et al. "Synthesis of Taxol from Baccatin IIII via an Oxazoline Intermediate," *Tetrahedron Lett.* 35(26): 4483–4484 (1994).

Kingston, et al. "Taxol: the chemistry and structure–activity relationships of a novel anticancer agent," *Trends Biotechnol.* 12(6): 222–7 (1994).

Kingston, et al. "The Chemistry of Taxol, A Clinically Useful Anticancer Agent," *J. Nat. Prod.,* 53(1):1–12 (1990).

Kingston, et al. "The chemistry of taxol," *Pharmacol Ther.* 52 (1):1–34 (1991).

Kitazume, et al. "Synthesis of optically active trifluorinated compounds: asymmetric Michael addition with hydrolytic enzymes," *Journal of Chemical Society, Chemical Communications* 1331–1333 (1986).

Klibanov, et al. "Asymmetric Transformations Catalyzed by Enzymes in Organic Solvents," *Acc. Chem. Res.* 23: 114–120 (1990).

Knani, et al. "Enzymatic polyesterification in organic media,"2. Enzyme–catalyzed synthesis of lateral–subtituted aliphatic polyesters and copolyesters, *J. Polymer Sci., part A—Polymer Chem.* 31(12): 2887–2897 (1993).

Kodelia, et al. "Enzymatic synthesis of butyryl–rutin ester in organic solvents and its cytogenetics effects in mammalian cells in culture," *Appl. Biochem. Biotech.* 44 (3): 205–212 (1994).

Kodelia, et al. "Studies on the reaction catalyzed by protease for the acylation of flavornoids in organic solvents," *Ann. New York Acad. Sci.* (Enzyme Eng. XI, D.S. Clark, D.A. Estell, eds) 672:451–457 (1992).

Kvittingen, et al. "Some aspects of biocatalysis in organic solvents," *Tetrahedron* 50(28): 8253–8274 (1994).

Lambusta, et al. "Lipase catalyzed acylation of phenols in organic solvents," *Ind. J. Chem.* Section B 32 (1): 58–60 (1993).

Li, et al. "Enzymes in organic chemistry. 1. Enantioselective hydrolysis of alpha –(acyloxy phosphonates by esterolytic enzymes," *Tetrahedron—Asymmetry* 4 (1): 109–120 (1993).

Ljunger, et al. "Lipase catalyzed acylation of glucose," *Biotechnol. Lett.* 16(11): 1167–1172 (1994).

Lopez, et al. "Enzymatic transesterification of alkyl 2,3, 4–tri–O–acyl–beta–D–xylopyranosides," *J. Carbohydrate Chem.* 12(2): 165–171 (1993).

Magri, et al. "Modified taxols, 4. Synthesis and biological activity of taxols modified in the side chain," *J Nat Prod.* 51(2): 298–306 (1988).

Mamber, et al. "Tubulin polymerization by paclitaxel (taxol) phosphate prodrugs after metabolic activation with alkaline phosphatase," *Pharmacol Exp Ther.* 274 (2):877–833 (1995).

Martin, et al. "Biocatalytic synthesis of sugar containing Poly(acrylate)–Based Hydrogels," *Macromolecules,* 25: 7081–7085 (1992).

Mathew, et al. "Synthesis and evaluation of some water–soluble prodrugs and derivatives of taxol with anti-tumor activity," *J Med Chem.* 35 (1):145–151 (1992).

Matzner, et al. "The Chemistry of Chloroformates," *Chem. Rev.* 64: 645 (1964).

McGuire, et al. "Taxol: a unique antineoplastic agent with significant activity in advanced ovarian epithelial neoplasms," *Ann Intern Med.* 111(4):273–279 (1989).

Mellado, et al. "Preparation and biological activity of taxol acetates," *Biochem Biophys Res Commun.* 124 (2):329–336 (1984).

Menedez, et al. "Acylation and alkoxycarbonylation of oximes through an enzymatic oximolysis reaction," *Synthesis—Stuttgart* 1: 72–74 (1993).

Miyanaga, et al. "Synthesis of aspartame precursor with an Immobilized Hermolysin in Mixed Organic Solvents," *Biotechnology & Bioengineering,* 46, 631–635 (1995).

Miyazawa, et al. "Lipase–catalyzed transesterification procedure for the resolution of non–protein amino acids," *Biotechnology Letters* 14 (9): 789–794 (1992).

Miyazawa, et al. "Resolution of racemic carboxylic acids via the lipase–catalyzed irreversible transesterification using vinyl esters—effects of alcohols as nucleophiles and organic solvents on enantioselectivity," *Biotechnology Letters* 14 (10): 941–946 (1992).

Mukesh, et al. "Lipase catalyzed esterification of isosorbide and sorbitol," *Biotechnology Letters* 15 (12): 1243–1246 (1993).

Murata, et al. "Lipase–catalyzed enantioselective synthesis of optically active mephobarbital, hexobarbital and febarbamate," *Chemical–Pharmaceutical Bulletin* 40(10): 2605–2609 (1992).

Naemura, et al. "Lipase YS–catalyzed enantioselective transesterification of alcohols of bicarbocyclic compounds," *Bull. Chem. Soc. Japan* 66(2):573–577 (1993).

Nagashima, et al. "Peptide synthesis by proteases in organic solvents: medium effect on substrate specificity," *Enzyme and Microbial Technology* 14 (10): 842–847 (1992).

Nasri, et al. "Increase of the potentialities of restriction endonucleases by specificity relaxation in the presence of organic solvents," *Ann. N.Y. Acad. Sci.* 542:255–265 (1988).

Natoli, et al. "Regioselective alcoholysis of flavonoid acetates with lipase in an organic solvent," *Journal of Organic Chemistry* 57 (21): 5776–5778 (1992).

Nicolaou, et al. "Design, synthesis and biological activity of protaxols" *Nature* 364: 464 (1993).

Nicolaou, et al. "Synthesis of C–2 Taxol Analogues" *Angew. Chem. Int. Ed. Eng.,* 33(15): 1581–1583 (1994).

Nicolaou, et al. "Total Synthesis of Taxol. 1. Retrosynthesis, Degradation, and Reconstitution," *JACS* 117:624–633 (1995).

Oguntimein, et al. "Lipase catalyzed synthesis of sugar ester in organic solvents," *Biotechnology Letters* 15 (2): 175–180 (1993).

Ojima, et al. "New and efficient approaches to the semisynthesis of taxol and its C–13 side chain analogs by means of β–lactam synthon method," *Tetrahedron* 48(34): 6985–7012 (1992).

Panza, et al. "Selective acylation 4,6–O–benzylidene glycopyranosides by enzymatic catalysis," *J. Carbohydrate Chem.* 12 (1):125–130 (1993).

Parida, et al. "Tailoring lipase specificity by solvent and substrate chemistries," *J. Org. Chem.* 58(12): 3238–3244 (1993).

Patel, et al. "Stereoselective enzymatic esterification of 3–benzoylthio–2 methylpropanoic acid," Ann. New York Acad. Sci (Enzyme Eng. XI, D.S. Clark, D.A. Estell, eds) 672: 415–424 (1992).

Pavel, et al "Enzymes in polymer chemistry. 7. Lipase–catalyzed esterification of carboxyl–terminated methacrylic oligomers and copolymers with isopropyl alcohol and 9–fluorenylmethanol," *Makromolekulare Chemie–Macromolecular Chemistry and Physics* 194(12): 3369–3376 (1993).

Persichetti, et al. "Cross–linked enzyme crystals (CLECs) of thermolysin in the synthesis of peptides," *JACS* 117(10): 2732–2737 (1995).

Pozo, et al. "Vinyl carbonates as novel alkoxycarbonylation reagents in enzymatic synthesis of carbonates," *Tetrahedron,* 48(31): 6477–6484 (1992).

Ringel, et al. "Taxol is converted to 7–epitaxol, a biologically active isomer, in cell culture medium," *J Pharmacol Exp Ther.* 242 (2):692–8 (1987).

Roberts, et al. "Enzymes as catalysts in organic synthesis," *NATO ASI Ser., Ser. A.* 178: 443–463 (1989).

Rowinsky, et al. "Taxol: a novel investigational antimicrotubule agent," *J Natl Cancer Inst.* 82 (15):1247–59 (1990).

Rowinsky, et al. "Taxol: the first of the taxanes, an important new class of antitumor agents," *Sem. Oncol.* 19(6): 646–662 (1992).

Sakurai, et al. "Control of enzyme enantioselectivity by the reaction medium," *Journal of the American Chemical Society* 110 (21): 7236–7237 (1998).

Schiff, et al. "Promotion of microtubule assembly in vitro by taxol," *Nature.* 277(5698): 665–7 (1979).

Schlotterbeck, et al. "Lipase–catalyzed monoacylation of fructose," *Biotechnology Letters* 15 (1): 61–64 (1993).

Schmidt & Effenberger, "C–glucosylarenes from O– $_D$–glucosyl trichloroacetimidates. Structure of bergenin derivatives," *Carbohydrate Research* 171:59–79 (1987).

Servi, et al. Baker's yeast as a regent in organic sythesis. *Synthesis* 1:1–25 (1990).

Sharma, et al. "Lipase catalyzed acetylation of carbohydrates," *Biotechnology Letters* 15(11): 1145–1146 (1993).

Sih, et al. "Microbial asymmetric catalysis–enantioselective reduction of ketones," *Angew. Chem. Int. Ed. Engl.* 23 (8): 570–578 (1984).

Sih, et al. "Microbial transformations in organic synthesis," Tech. Chem. (N.Y.), 10(Appl. Biochem. Syst. Org. Chem., Part 1)69–106 (1976).

Stahl, et al. "Induced steroselectivity and substrate selectivity of bio–imprinted alpha–chymotrypsin in anhydrous organic media," *JACS* 113 (24): 9366–9368 (1991).

Stahl, et al. "The synthesis of a D–amino acid ester in an organic media with alpha–chymotrypsin modified by a bio–imprinting procedure," *Biotechnology Letters* 12(3): 161–166 (1990).

Tanaka, et al. "Bioconversion of nonnatural organic compounds—esterification and dehydrogenation of organosilicon compounds," Ann. New York Acad. Sci (Enzyme Eng. XI, D.S. Clark, D.A. Estell, eds) 672: 431–435 (1992).

Tawaki, et al. "Chemoselectivity of enzymes in anhydrous media is strongly solvent dependent," *Biocatalysis* 8(1): 3–19 (1993).

Terradas, et al. "Marked dependence of enzyme prochiral selectivity on the solvent," *JACS* 115 (2): 390–396 (1993).

Therisod, et al. "Facile enzymatic preparation of monoacylated Sugars in Pyridine," *JACS* 108: 5638–5640 (1986).

Thompson, et al. "Microbial biotransformations of nitriles," *Chem. Br.* 24(9): 900 (1988).

Tsai, et al. "Effect of solvent on enantioselective esterification of naproxen by lipase with trimethylsilyl methanol," *Biotechnology and Bioengineering* 43(1); 64–68 (1994).

Ueda et al. "Synthesis and antitumor evaluation of 2'-oxycarbonylpaclitaxels (paclitaxel–2'carbonates)," *Bioorg. Med. Chem. Lett.*, 4(15): 1861–1864 (1994).

Ueda, et al. "Novel, water–soluble phosphate derivatives of 2'-ethoxy carbonylpaclitaxel as potential drodrugs of paclitaxel: synthesis and antitumor evaluation," *Bioorg. Med. Chem. Lett* 5(3): 247–252 (1995).

Uejima, et al. "Efficient kinetic resolution of orangosilicon compounds by steroselective esterification with hydrolases in organic solvent," *Appl. Microbial Biotech.* 38(4): 482–486 (1993).

Vazquez–Duhalt, et al. "Lignin peroxidase oxidation of aromatic compounds in systems containing organic solvents," *Applied and Environmental Microbiology* 60(2): 459–466 (1994).

Wagner, et al. "Synthesis of uncommon wax esters with immobilized lipases," Ann. New York Acad. Sci. (Enzyme Eng. XI, D.S. Clark, D.A. Estell, eds) 672: 484–491 (1992).

Wang, et al. "Regioselective oxidative polymerization of 1,5–dihydroxynaphthalene catalyzed by bilirubin oxidase in a water–organic solvent mixed solution," *Journal of Polymer Science Part A—Polymer Chemistry* 31 (11) 2855–2861 (1993).

Ward, et al. "Reductive biotransformations of organic compounds by cells or enzymes of yeast," *Enzyme Microb. Technol.* 12 (7): 482–493 (1990).

Wescott, et al. "Solvent variation inverts substrate specificity of an enzyme," *JACS* 115 (5): 1629–1631 (1993).

Yamada, et al. "Microbial and enzymatic processes for the production of biologically and chemically useful compounds," *Angew. Chem. Int. Ed. Engl.* 27 (5): 622–642 (1988).

Zaks, et al., "Substrate specificity of enzymes in organic solvents vs. water is reversed," *JACS* 108: 2767–2768: (1986).

Zhao, et al. "Modified taxols, 6. Preparation of Water–Soluble Prodrugs of Taxol," *J. Natl. Prod.* 54(6): 1607–1611 (1991).

* cited by examiner

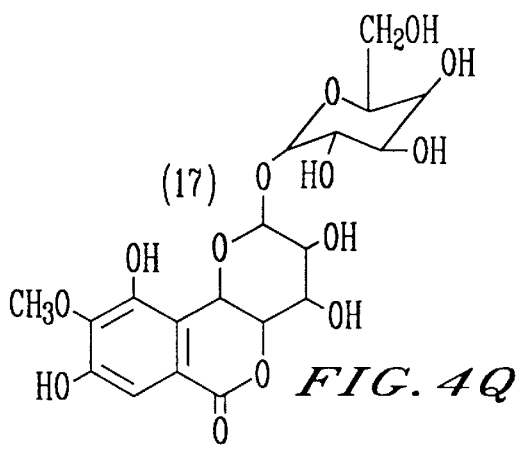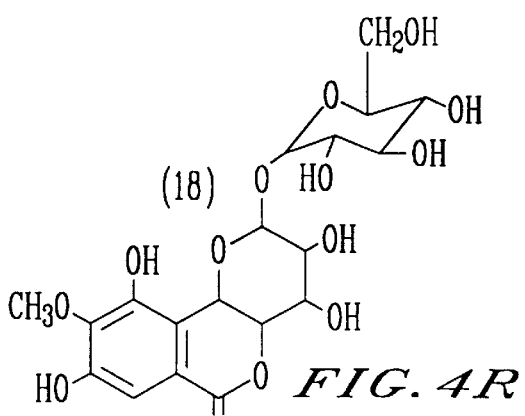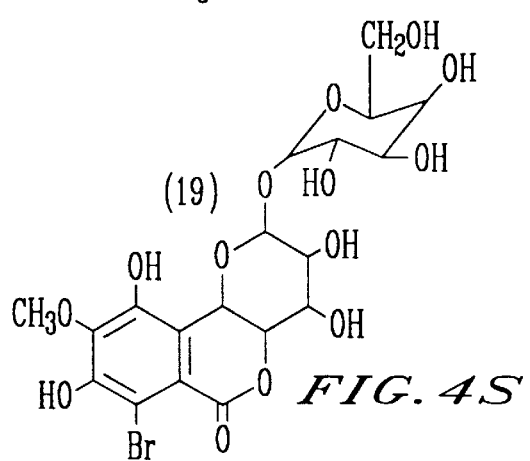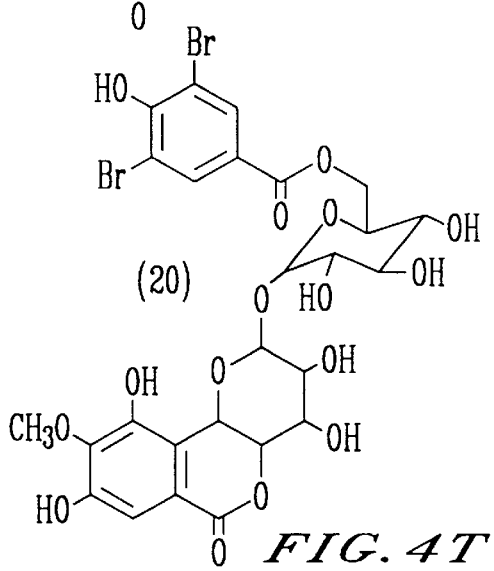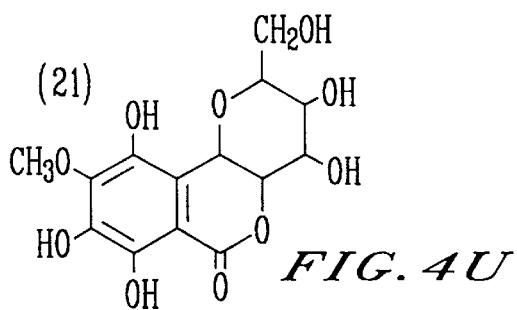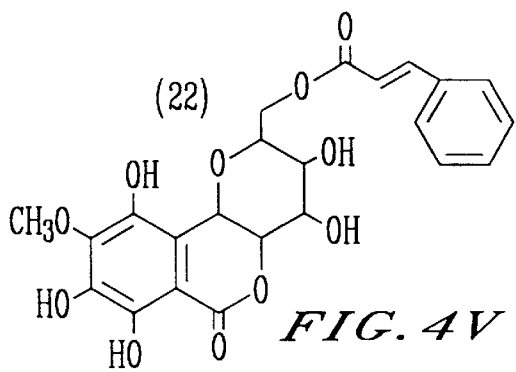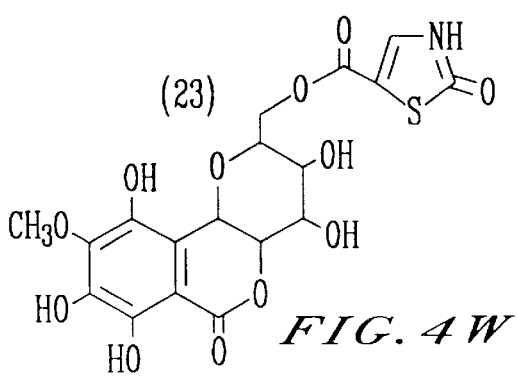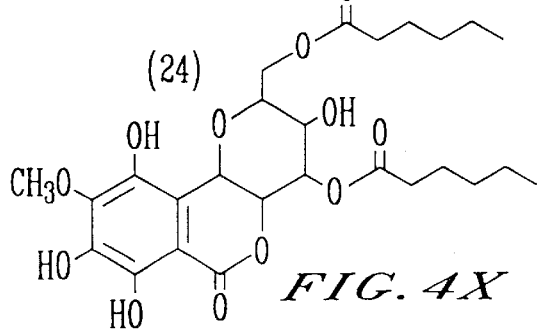

TAXOL DERIVATIVES

This application is a continuation of U.S. Ser. No. 09/091,833 filed Jun. 29, 1998 now U.S. Pat. No. 6,136,961, which is a 371 of International Application No. PCT/US96/14573 filed Sep. 11, 1996, which claims priority to U.S. Provisional Application Serial No. 60/003,661 filed Sep. 11, 1995.

BACKGROUND OF THE INVENTION

1. Field of the Invention

This invention is in the field of biologically active compounds.

2. Discussion of the Background

The prior art is replete with examples of chemically, microbially, or enzymatically synthesizing compounds with biological activity. The goal of these efforts is the discovery of new and improved pharmaceutical compounds.

The discovery of new pharmaceutical compounds is for the most part a trial and error process. So many diverse factors constitute an effective pharmaceutical compound that it is extremely difficult to reduce the discovery process to a systematic approach. Typically, thousands of organic compounds must be isolated from biological sources or chemically synthesized and tested before a pharmaceutical compound is found.

Synthesizing and testing new compounds for biological activity, which is the first step in identifying a new synthetic drug, is a time consuming and expensive undertaking. Typically, compounds must by synthesized, purified, tested and quantitatively compared to other compounds in order to identify active compounds or identify compounds with optimal activity. The synthesis of new compounds is accomplished for the most part using standard chemical methods. Such methods provide for the synthesis of virtually any type of organic compound; however, because chemical reactions are non-specific, these syntheses require numerous steps and multiple purifications before a final compound is produced and ready for testing.

New biological and chemical approaches have recently been developed which provide for the synthesis and screening of large libraries of small peptides and oligonucleotides. These methods provide for the synthesis of a broad range of chemical compounds and provide the means to potentially identify biologically active compounds. The chemistries for synthesizing such large numbers of these natural and non-naturally occurring polymeric compounds is complicated, but manageable because each compound is synthesized with the same set of chemical protocols, the difference being the random order in which amino acids or nucleotides are introduced into the reaction sequence.

The prior art Is replete with examples showing enzymatic conversion of non-physiological substances under many conditions.

REFERENCES DEMONSTRATING THAT ENZYME SPECIFICITY CAN BE CHANGED/TAILORED

1. Zaks, A. and Klibanov, A. M. Substrate specificity of enzymes in organic solvents vs. water is reversed. Journal of the American Chemical Society 108 2767–2768, 1986.
2. Ferjancic, A., Puigserver, A. and Gaertner, H. Unusual specificity of PEG-modified thermolysin in peptide synthesis catalyzed in organic solvents. Biotechnology Letters 10 (2) 101–106, 1988.
3. Nasri, M. and Thomas, D. Increase of the potentialities of restriction endonucleases by specificity relaxation in the presence of organic solvents. Ann. N.Y. Acad. Sci. 542 255–265, 1988.
4. Stahl, M., Mansson, M. O. and Mosbach, K. The synthesis of a D-amino acid ester in an organic media with chymotrypsin modified by a bio-imprinting procedure. Biotechnology Letters 12 (3) 161–166, 1990.
5. Stahl, M., Jeppsson-Wistrand, U., Mansson, M. O. and Mosbach, K. Induced stereoselectivity and substrate selectivity of bio-imprinted a-chymotrypsin in anhydrous organic media. Journal of the American Chemical Society 113 (24) 9366–9368, 1991.
6. Gololobov, M. Y., Voyushina, T. L., Stepanov, V. M. and Adlercreutz, P. Organic solvent changes the chymotrypsin specificity with respect to nucleophiles. FEBS Letters 307 (3) 309–312, 1992.
7. Hertmanni, P., Pourplanche, C. and Larreta-Garde, V. Orientation of enzyme catalysis and specificity by water-soluble additives. Ann. New York Acad. Sci. (Enzyme Eng. XI, D. S. Clark, D. A. Estell, eds) 672 329–335, 1992.
8. Cabezas, M. J., del Campo, C., Llama, E., Sinisterra, J. V. and Gaertner, H. Organic reactions catalyzed by modified enzymes. 1. Alteration of the substrate specificity of a-chymotrypsin by the modification process. Journal of Molecular Catalysis 71 (2) 261–278, 1992.
9. Nagashima, T., Watanabe, A. and Kise, H. Peptide synthesis by proteases in organic solvents: medium effect on substrate specificity. Enzyme and Microbial Technology 14 (10) 842–847, 1992.
10. Parida, S. and Dordick, J. S. Tailoring lipase specificity by solvent and substrate chemistries, J. Org. Chem. 58 (12) 3238–3244, 1993.
11. Tawaki, S. and Klibanov, A. M. Chemoselectivity of enzymes in anhydrous media is strongly solvent dependent. Biocatalysis 8 (1) 3–19, 1993.
12. Wescott, C. F. and Klibanov, A. M. Solvent variation inverts substrate specificity of an enzyme. JACS 115 (5) 1629–1631, 1993.

REFERENCES DEMONSTRATING THAT ENZYME ENANTIOSELECTIVITY CAN BE CHANGED/TAILORED

1. Sakurai, T., Margolin, A. L., Russell, A. J. and Klibanov, A. M. Control of enzyme enantioselectivity by the reaction medium. Journal of the American Chemical Society 110 (21) 7236–7237, 1988.
2. Fitzpatrick, P. A. and Klibanov, A. M. How can the solvent affect enzyme enantioselectivity? Journal of the American Chemical Society 113 (8) 3166–3171, 1991.
3. Hult, K. and Norin, T. Enantioselectivity of some lipases—control and prediction. Pure and Applied Chemistry 64 (8) 1129–1134, 1992.
4. Miyazawa, T., Kurita, S., Ueji, S., Yamada, T. and Kuwata, S. Resolution of racemic carboxylic acids via the lipase-catalyzed irreversible transesterification using vinyl esters—effects of alcohols as nucleophiles and organic solvents on enantioselectivity. Biotechnology Letters 14 (10) 941–946, 1992.
5. Tawaki, S. and Klibanov, A. M. Inversion of enzyme enantioselectivity mediated by the solvent. Journal of the American Chemical Society 114 (5) 1882–1884, 1992.
6. Ueji, S., Fujino, R., Okubo, N., Miyazawa, T., Kurita, S., Kitadani, M. and Muromatsu, A. Solvent-induced inversion of enantioselectivity in lipase-catalyzed esterification of 2-phenoxypropionic acids. Biotechnology Letters 14 (3) 163–168, 1992.

7. Terradas, F., Testonhenry, M., Fitzpatrick, P. A. and Klibanov, A. M. Marked dependence of enzyme prochiral selectivity on the solvent. Journal of the American Chemical Society 115 (2) 390–396, 1993.
8. Herradon, B. Biocatalytic synthesis of chiral polyoxygenated compounds: effect of the solvent on the enantioselectivity of lipase catalyzed transesterifications in organic solvents. Synlett 2 108–110, 1993.

REFERENCES DEMONSTRATING THE ABILITY OF ENZYMES TO CONVERT UNNATURAL SUBSTRATES

1. Bianchi, D., Cesti, P., Golini, P., Spezia, S., Garavaglia, C. and Mirenna, L. Enzymatic preparation of optically active fungicide intermediates in aqueous and in organic media. Pure and Applied Chemistry 64 (8) 1073–1078, 1992.
2. Natoli, M., Nicolosi, G. and Piattelli, M. Regioselective alcoholysis of flavonoid acetates with lipase in an organic solvent. Journal of Organic Chemistry 57 (21) 5776–5778, 1992.
3. Izumi, T., Tamura, F. and Sasaki, K. Enzymatic kinetic resolution of <4> (1,2)ferrocenophane derivatives. Bulletin of the Chemical Society of Japan 65 (10) 2784–2788, 1992.
4. Miyazawa, T., Mio, M., Watanabe, Y., Yamada, T. and Kuwata, S. Lipase-catalyzed transesterification procedure for the resolution of non-protein amino acids. Biotechnology Letters 14 (9) 789–794, 1992.
5. Murata, M., Uchida, H. and Achiwa, K. Lipase-catalyzed enantioselective synthesis of optically active mephobarbital, hexobarbital and febarbamate. Chemical-Pharmaceutical Bulletin 40 (10) 2605–2609, 1992.
6. Johnson, C. R., Golebiowski, A. and Steensma, D. H. Enzymatic asymmetrization in organic media—synthesis of unnatural glucose from cycloheptatriene. Journal of the American Chemical Society 114 (24) 9414–9418, 1992.
7. Cruces, M. A., Otero, C., Bernabe, M., Martinlomas, M. and Ballesteros, A. Enzymatic preparation of acylated sucroses. Ann. New York Acad. Sci. (Enzyme Eng. XI, D. S. Clark, D. A. Estell, eds) 672 436–443, 1992.
8. Tanaka, A., Fukui, T., Uejima, A., Zong, M. H. and Kawamoto, T. Bioconversion of nonnatural organic compounds—esterification and dehydrogenation of organosilicon compounds. Ann. New York Acad. Sci (Enzyme Eng. XI, D. S. Clark, D. A. Estell, eds) 672 431–435, 1992.
9. Kodelia, G. and Kolisis, F. N. Studies on the reaction catalyzed by protease for the acylation of flavonoids in organic solvents. Ann. New York Acad. Sci. (Enzyme Eng. XI, D. S. Clark, D. A. Estell, eds) 672 451–457, 1992.
10. Wagner, F., Kleppe, F., Lokotsch, W., Ziemann, A. and Lang, S. Synthesis of uncommon wax esters with immobilized lipases. Ann. New York Acad. Sci. (Enzyme Eng. XI, D. S. Clark, D. A. Estell, eds) 672 484–491, 1992.
11. Patel. R. N., Howell, J. M., Banerjee, A., Fortney, K. F. and Szarka, L. J. Stereoselective enzymatic esterification of 3-benzoylthio-2-methylpropanoic acid. Ann. New York Acad. Sci (Enzyme Eng. XI, D. S. Clark, D. A. Estell, eds) 672 415–424, 1992.
12. Bergbreiter, D. E. and Momongan, M. Asymmetric synthesis of organometallic reagents using enzymatic methods. Applied Biochemistry and Biotechnology 32 1–3 55–72, 1992.
13. Carretero, J. C. and Dominguez, E. Lipase-catalyzed kinetic resolution of—hydroxy phenyl sulfones. Journal of Organic Chemistry 57 (14) 3867–3873, 1992.
14. Johnson, C. R., Adams, J. P., Bis, S. J., Dejong, R. L., Golebiowski, A., Medich, J. R., Penning, T. D., Senanayake, C. H., Steensma, D. H. and Vanzandt, M. C. Applications of enzymes in the synthesis of bioactive polyols. Indian Journal of Chemistry Section B—Organic Chemistry Including Medicinal Chemistry 32 (1) 140–144, 1993.
15. Fabre, J., Betbeder, D., Paul, F., Monsan, P. and Perie, J. Regiospecific enzymic acylation of butyl a-D-glucopyranoside. Carbohydrate Research 243 (2) 407–411, 1993.
16. Bianchi, D., Cesti, P., Golini, P., Spezia, S., Garavaglia, C. and Mirenna, L. Enzymatic preparation of optically active fungicide intermediates in aqueous and in organic media. Indian Journal of Chemistry Section B—Organic Chemistry Including Medicinal Chemistry 32 (1) 176–180, 1993.
17. Kanerva, L. T. and Sundholm, O. Lipase catalysis in the resolution of racemic intermediates of diltiazem synthesis in organic solvents. Journal of the Chemical Society—Perkin Transactions I. 13 1385–1389, 1993.
18. Ikeda, I. and Klibanov, A. M. Lipase-catalyzed acylation of sugars solubilized in hydrophobic solvents by complexation. Biotechnology and Bioengineering 42 (6) 788–791, 1993.
19. Hyun, C. K., Kim, J. H. and Ryu, D. D. Y. Enhancement effect of water activity on enzymatic synthesis of cephalexin. Biotechnology and Bioengineering 42 (7) 800–806, 1993.
20. Panza, L., Luisetti, M., Crociati, E. and Riva, S. Selective acylation of 4,6-O-benzylidene glycopyranosides by enzymatic catalysis. J. Carbohydrate Chem. 12 (1) 125–130, 1993.
21. Wang, L., Kobatake, E., Ikariyama, Y. and Aizawa, M. Regioselective oxidative polymerization of 1,5-dihydroxynaphthalene catalyzed by bilirubin oxidase in a water-organic solvent mixed solution. Journal of Polymer Science Part A—Polymer Chemistry 31 (11) 2855–2861, 1993.
22. Knani, D. and Kohn, D. H. Enzymatic polyesterification in organic media. 2. Enzyme-catalyzed synthesis of lateral-substituted aliphatic polyesters and copolyesters. J. Polymer Sci., Part A—Polymer Chem. 31 (12) 2887–2897, 1993.
23. Kanerva, L. T. and Sundholm O. Enzymatic acylation in the resolution of methyl threo-2-hydroxy-3-(4-methoxyphenyl)-3-(2-x-phenylthio)propionates in organic solvents. Journal of the Chemical Society—Perkin Transactions I 20 2407–2410, 1993.
24. Sharma, A. and Chattopadhyay, S. Lipase catalyzed acetylation of carbohydrates. Biotechnology Letters 15 (11) 1145–1146, 1993.
25. Pavel, K. and Ritter, H. Enzymes in polymer chemistry. 7. Lipase-catalyzed esterification of carboxyl-terminated methacrylic oligomers and copolymers with isopropyl alcohol and 9-fluorenylmethanol. Makromolekulare Chemie-Macromolecular Chemistry and Physics 194 (12) 3369–3376, 1993.
26. Uejima, A., Fukui, T., Fukusaki, E., Omata, T., Kawamoto, T., Sonomoto, K. and Tanaka, A. Efficient kinetic resolution of organosilicon compounds by stereoselective esterification with hydrolases in organic solvent. Appl. Microbial. Biotech. 38 (4) 482–486, 1993.
27. Mukesh, D., Sheth, D., Mokashi, A., Wagh, J., Tilak, J. M., Banerji, A. A. and Thakkar, K. R. Lipase catalyzed esterification of isosorbide and sorbitol. Biotechnology Letters 15 (12) 1243–1246, 1993.

28. Baldessari, A., Iglesias, L. E. and Gros, E. G. Regioselective acylation of 3-mercaptopropane-1,2-diol by lipase-catalyzed transesterification. Journal of Chemical Research—S 9 382–383, 1993.
29. De Goede, A. T. J. W., Benckhuijsen, W., van Rantwijk, F., Maat, L. and van Bekkum, H. Selective lipase-catalyzed 6-O-acylation of alkyl a-D-glucopyranosides using functionalized ethyl esters. Recueil Des Travaux Chimiques Des Pays Bas—Journal of the Royal Netherlands Chemical Society 112 (11) 567–572, 1993.
30. Menendez, E. and Gotor, V. Acylation and alkoxycarbonylation of oximes through an enzymatic oximolysis reaction. Synthesis—Stuttgart 1 72–74, 1993.
31. Li, Y. F. and Hammerschmidt, F. Enzymes in organic chemistry. 1. Enantioselective hydrolysis of a-(acyloxy) phosphonates by esterolytic enzymes. Tetrahedron—Asymmetry 4 (1) 109–120, 1993.
32. Schlotterbeck, A., Lang, S., Wray, V. and Wagner, F. Lipase-catalyzed monoacylation of fructose. Biotechnology Letters 15 (1) 61–64, 1993.
33. Frykman, H., Ohrner, N., Norin, T. and Hult, K. S-Ethyl thiooctanoate as acyl donor in lipase catalyzed resolution of secondary alcohols. Tetrahedron Letters 34 (8) 1367–1370, 1993.
34. Oguntimein, G. B., Erdmann, H. and Schmid, R. D. Lipase catalyzed synthesis of sugar ester in organic solvents. Biotechnology Letters 15 (2) 175–180, 1993.
35. Lopez, R., Perez, C., Fernandez-Mayorales, A. and Conde, S. Enzymatic transesterification of alkyl 2,3,4-tri-O-acyl-beta-D-xylopyranosides. J. Carbohydrate Chem. 12 (2) 165–171, 1993.
36. Naemura, K., Ida. H. and Fukuda, R. Lipase YS-catalyzed enantioselective transesterification of alcohols of bicarbocyclic compounds. Bull. Chem. Soc. Japan 66 (2) 573–577, 1993.
37. Lambusta, D., Nicolosi, G., Piattelli, M. and Sanfilippo, C. Lipase catalyzed acylation of phenols in organic solvents. Ind. J. Chem. Section B 32 (1) 58–60, 1993.
38. Astorga, C., Rebolledo, F. and Gotor, V. Enzymatic hydrazinolysis of diesters and synthesis of N-aminosuccinimide derivatives. Synthesis—Stuttgart 3 287–289, 1993.
39. Fukui, T., Kawamoto, T. and Tanaka, A. Enzymatic preparation of optically active silylmethanol derivatives having a stereogenic silicon atom by hydrolase-catalyzed enantioselective esterification. Tetrahedron—Asymmetry 5 (1) 73–82, 1994.
40. Vazquez-Duhalt, R., Westlake, D. W. S. and Fedorak, P. M. Lignin peroxidase oxidation of aromatic compounds in systems containing organic solvents. Applied and Environmental Microbiology 60 (2) 459–466, 1994.
41. Kodelia, G., Athanasiou, K. and Kolisis, F. N. Enzymatic synthesis of butyryl-rutin ester in organic solvents and its cytogenetic effects in mammalian cells in culture. Appl. Biochem. Biotech. 44 (3) 205–212, 1994.
42. Tsai, S. W. and Wei, H. J. Effect of solvent on enantioselective esterification of naproxen by lipase with trimethylsilyl methanol. Biotechnology and Bioengineering 43 (1) 64–68, 1994.
43. Athawale, V. D. and Gaonkar, S. R. Enzymatic synthesis of polyesters by lipase catalyzed polytransesterification. Biotechnology Letters 16 (2) 149–154, 1994.
44. Janssen, G. G. and Haas, M. J. Lipase-catalyzed synthesis of oleic acid esters of polyethylene glycol 400. Biotechnology Letters 16 (2) 163–168, 1994.
45. Kitazuma, T., Ikeya, T. and Murata, K. Synthesis of optically active trifluorinated compounds: asymmetric Michael additional with hydrolytic enzymes. Journal of Chemical Society, Chemical Communications 1331, 1986.

REFERENCES DEMONSTRATING MICROBIAL TRANSFORMATIONS

1. Holland, H. L. Fungi as reagents in organic synthesis: preparation of some metabolites of prostanoids, steroids, and other natural products. Rev. Latinoam. Quim., (1st Spec. Suppl.), 318–329, 1990.
2. Sih, C. J. and Rosazza, J. P. Microbial transformations in organic synthesis. Tech. Chem. N.Y.), 10 (Appl. Biochem. Syst. Org. Chem., Part 1) 69–106,1976.
3. Sih, C. J. and Chen, C. S. Microbial asymmetric catalysis-enantioselective reduction of ketones. Angew. Chem. Int. Ed. Engl. 23 (8) 570–578, 1984.
4. Thompson, L. A. and Knowles, C. J., Linton, E. A. and Wyatt, J. M. Microbial biotransformations of nitriles. Chem. Br. 24 (9) 900, 1988.
5. Servi, S. Baker's yeast as a reagent in organic synthesis. Synthesis 1 1–25, 1990.
6. Csuk, R. and Glanzer, B. I. Baker's yeast mediated transformations in organic chemistry. Chem. Rev. 91 (1) 49–97, 1991.
7. Roberts, S. M., Wiggins, K. and Casy, G. Whole cells and isolated enzymes in organic synthesis. Wiley, New York, 1992.
8. Ward, O. P. and Young, C. S. Reductive biotransformations of organic compounds by cells or enzymes of yeast. Enzyme Microb. Technol. 12 (7) 482–493, 1990.

REVIEWS

1. Jones, J. B. Enzymes in organic synthesis. Tetrahedron 42 (13) 3351–3405, 1986.
2. Yamada, H. and Shimizu, S. Microbial and enzymatic processes for the production of biologically and chemically useful compounds. Angew. Chem. Int. Ed. Engl. 27 (5) 622–642, 1988.
3. Roberts, S. M. Enzymes as catalysts in organic synthesis. NATO ASI Ser., Ser. A. 178 443–463, 1989.
4. Chen, S. S. and Sih, C. J. General aspects and optimization of enantioselective biocatalysis in organic solvents: the use of lipases. Angew. Chem (Int. Ed. Engl. 28, n 6 695–707) 101 (6) 711–724, 1989.

Taxol[1], a diterpenold originally isolated from the bark of the Pacific yew, Taxus brevifolia, is a powerful antimitotic agent[2] that acts by promoting tubulin assembly into stable aggregated structures. Taxol has shown tremendous potential as an anticancer compound. Indeed, it is now used for the treatment of refractory ovarian cancer[3], and clinical trials are encouraging for the treatment of breast, lung[4], head, and neck[5] cancers. Because of its broad antitumor activity and limited availability, numerous studies have been devoted to the synthesis[6] (including semisynthesis from the baccatin III nucleus[7]), mechanism[1], and structure-activity relationships of taxol and protaxols.[1a,1d,8] Despite such intense investigation, the use of taxol as an anticancer drug is compromised by its poor aqueous solubility. For this reason, a number of water-soluble taxol prodrugs have been synthesized that contain hydrophilic or charged functionalities attached to specific sites on the taxol molecule.[9]

Acylation at the 2' position can be a very effective strategy for improving the water solubility of taxol.[9a-e] Interestingly, acylation of the C-2' hydroxyl eliminates microtube stabilization but not cytotoxicity, which is consistent with the hydrolytic regeneration of taxol from protaxol within the cell.[8] Water soluble protaxols modified at the 2' position include arylsulfonyl ethoxycarbonates and thiodiglycolic esters synthesized by Nicolaou et al.[9a], the most soluble of which were 100 to 1000 times more soluble than taxol.

Accordingly, taxol derivatives with improved solubiity are sought.

SUMMARY OF THE INVENTION

According to one embodiment of the present invention is taxol-2'-adipate derivatives.

According to another embodiment of the present invention is derivatives of bergenin.

According to another embodiment of the present invention is derivatives erythromycyin.

According to another embodiment of the present invention is a library of derivatives based on 2,3-(methylenedioxy)benzaldehyde.

According to another embodiment of the present invention is a library of derivatives based on (±)-(2-endo,3-exo)-bicyclo[2.2.2]octo-5-ene-2,3-dimethanol.

According to another embodiment of the present invention is a library of derivatives based on adenosine.

These and other objects of the present invention are made possible by the taxol-2'-adipate derivatives of the formula.

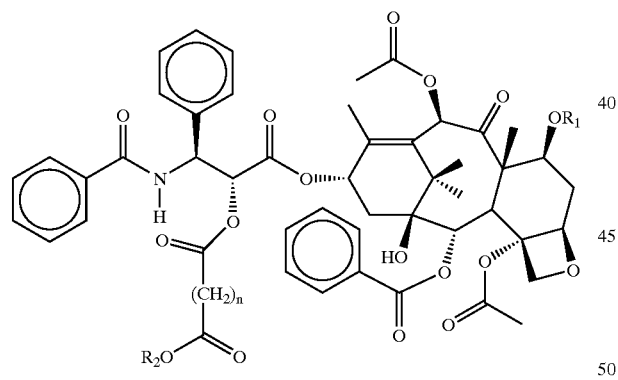

wherein:

$R_1$ is hydrogen, $C_{1-10}$ alkyl ester, halosubstituted $C_{1-10}$ alkyl ester, or $CO(CH_2)_nCOR_2$ where n is an integer of 2–10 and $R_3$ is hydrogen, $C_{1-10}$ alkyl or $C_{1-10}$ alkenyl;

n is an integer of 2–10; and $R_2$ is hydrogen, $C_{1-10}$ alkyl, $C_{1-10}$ alkenyl, or a 6 substituted saccharide compound selected from the group consisting of glucose, galactose, allose, altrose, mannose, gulose, idose, talose, lactose, cellobiose, sucrose, fructose and maltose, in the open or pyranose form.

These and other objects of the present invention are made possible by derivatives of bergenin, of the formula

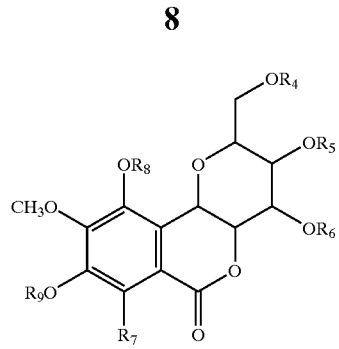

wherein $R_4$, $R_5$, and $R_6$ are each independently hydrogen, $C_{1-10}$ alkyl ester, $C_{1-10}$ alkyl substituted $C_{1-10}$ alkyl ester, halosubstituted $C_{1-10}$ alkyl ester, $C_{6-20}$ aralkyl ester, halo substituted $C_{6-20}$ aralkyl ester, $C_{6-20}$ aralkenyl ester, a 1 substituted saccharide compound selected from the group consisting of glucose, galactose, allose, altrose, mannose, gulose, idose, talose, lactose, cellobiose, sucrose, fructose, deoxynojirimycin, N-acetyl glucoseamine, N-acetyl galactoseamine, and maltose, or $CO(CH_2)_nCOR_{10}$ where n is an integer of 2–10; and $R_{10}$ is OH, $C_{1-10}$ alkoxy, $C_{1-10}$ alkenyloxy, a 6 substituted saccharide compound selected from the group consisting of glucose, galactose, allose, altrose, mannose, gulose, idose, talose, lactose, cellobiose, sucrose, fructose and maltose, in the open or pyranose form, $NR_{11}R_{12}$ where $R_{11}$ and $R_{12}$ are each independently hydrogen, $C_{1-10}$ alkyl, substitued $C_{1-10}$ alkyl substitued with $C_{1-10}$ alkyl, $C_{6-20}$ aryl or halogen;

$R_7$ is H, OH, F, Cl, Br, or I;

$R_8$ and $R_9$ are each independently hydrogen or $C_{1-10}$ alkyl, provided that when $R_7$ is H, $R_4$, $R_5$ and $R_6$ are not each hydrogen.

These and other objects of the present invention are made possible by erythromycin derivatives of the formula

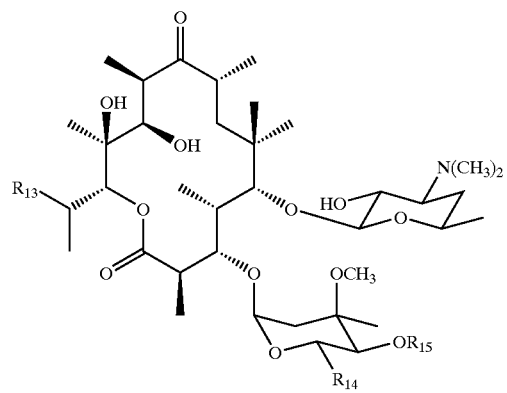

wherein $R_{13}$ is hydrogen or OH;

$R_{14}$ is $CH_3$ or $CO_2H$; and $R_{15}$ is hydrogen or $CO(CH_2)_nCOR_{16}$ where n is an integer of 2–10; and $R_{16}$ is OH, $C_{1-10}$ alkoxy, $C_{1-10}$ alkenyloxy, a 6 substituted saccharide compound selected from the group consisting of glucose, galactose, allose, altrose, mannose, gulose, idose, talose, lactose, cellobiose, sucrose, fructose and maltose, $NR_{17}R_{18}$ where $R_{17}$ and $R_{18}$ are each independently hydrogen, $C_{1-10}$ alkyl, substitued $C_{1-10}$ alkyl substitued with $C_{1-10}$ alkyl, $C_{6-20}$ aryl or halogen; provided that when $R_{13}$ and $R_{15}$ are each hydrogen, $R_{14}$ is not $CH_3$.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERED EMBODIMENTS

Figure 1:
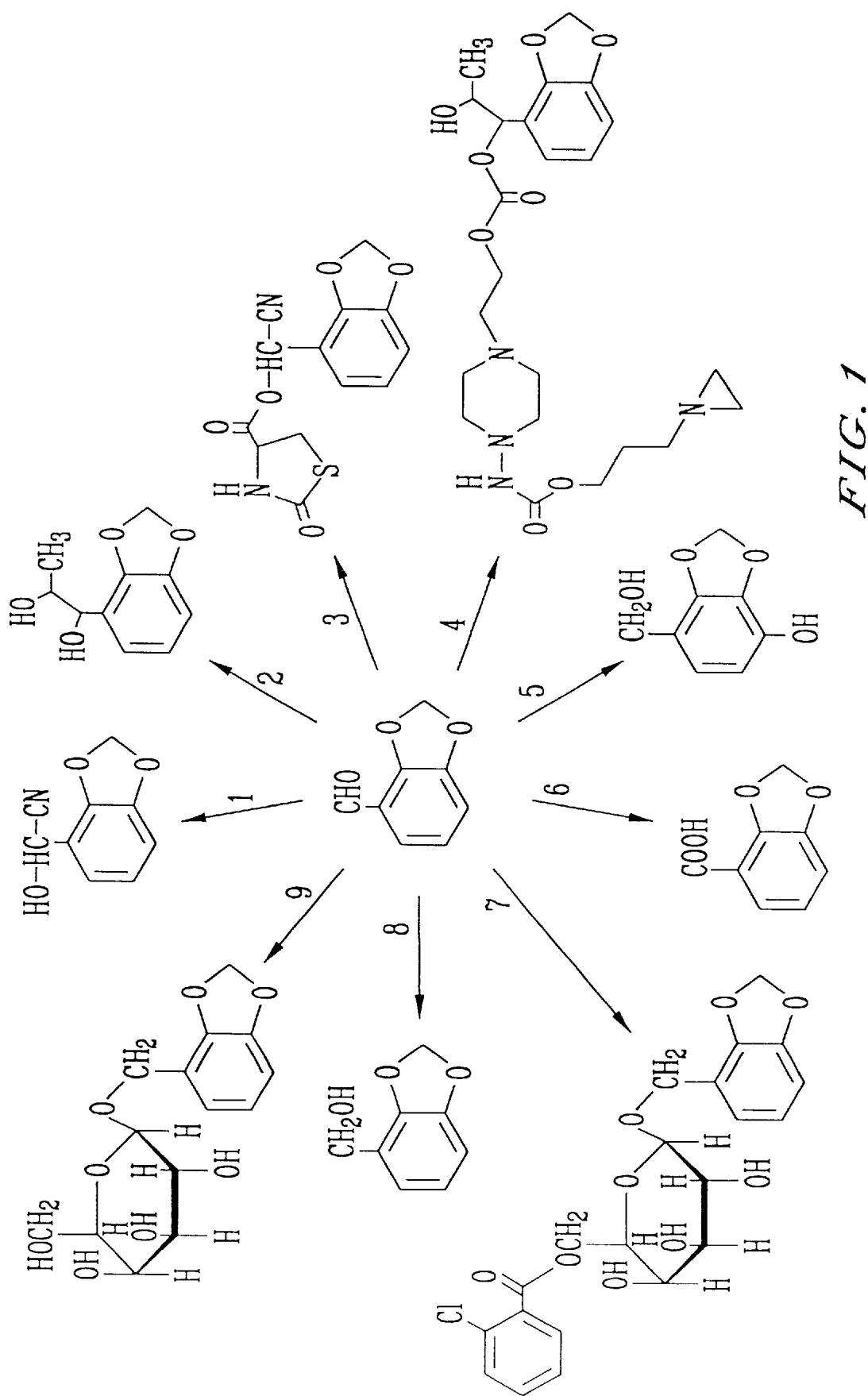
FIG. 1 describes a library of derivatives based on 2,3-(methylenedioxy)benzaldehyde.

The present invention is directed to organic compounds from a starting compound which exhibit biological activity. This has been accomplished through the use of highly specific biocatalytic reactions.

Enzymes are highly selective catalysts. Their hallmark is the ability to catalyze reactions with exquisite stereo-, regio-, and chemo-selectivities that are unparalleled in conventional synthetic chemistry. Moreover, enzymes are remarkably versatile. They can be tailored to function in organic solvents, operate at extreme pH's and temperatures, and catalyze reactions with compounds that are structurally unrelated to their natural, physiological substrates.

Enzymes are reactive toward a wide range of natural and unnatural substrates, thus enabling the modification of virtually any organic lead compound. Moreover, unlike traditional chemical catalysts, enzymes are highly enantio- and regio-selective. The high degree of functional group specificity exhibited by enzymes enables one to keep track of each reaction in a synthetic sequence leading to a new active compound. Enzymes are also capable of catalyzing many diverse reactions unrelated to their physiological function in nature. For example, peroxidases catalyze the oxidation of phenols by hydrogen peroxide. Peroxidases can also catalyze hydroxylation reactions that are not related to the native function of the enzyme. Other examples are proteases which catalyze the breakdown of polypeptides. In organic solution some proteases can also acylate sugars, a function unrelated to the native function of these enzymes.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds. Each biocatalyst is specific for one functional group, or several related functional groups, and can react with many starting compounds containing this functional group.

The biocatalytic reactions can be used to produce a population of derivatives from a single starting compound. These derivatives can be subjected to another round of biocatalytic reactions to produce a second population of derivative compounds. Thousands of variations of the original compound can be produced with each iteration of biocatalytic derivatization.

More specifically, the enzymatic reactions may be conducted with a group of enzymes that react with distinct structural moieties found within the structure of a starting compound. Each enzyme is specific for one structural moiety or a group of related structural moieties. Furthermore, each enzyme reacts with many different starting compounds which contain the distinct structural moiety.

In accordance with the present invention, the starting point of the present work was to identify an appropriate enzyme catalyst suitable for acylation of taxol in the first step. After testing a wide range of enzymes and solvents[12], thermolysin (an extracellular protease from *Bacillus thermoproteolyticus rokko*) suspended in anhydrous tert-amyl alcohol was identified to be the most effective catalyst for taxol acylation.[13] In particular, this enzyme catalyzed acylation of taxol with a bifunctional acyl donor, divinyl adipate, as determined by TLC and HPLC.[14] The reactivity of thermolysin toward taxol was enhanced ca. 20-fold by lyophilizing the enzyme in the presence of KCl prior to use.[15] Using the salt-activated enzyme preparation (5.7 mg/ml protein), ca. 90% conversion of taxol (14 mM solution) was obtained in 96 h in the presence of 45 mM divinyl adipate. Following termination of the reaction[16], two products were isolated from the reaction mixture via preparative HPLC. The identities of these products were determined by mass spectroscopy and $^1$H-NMR to se taxol 2'-vinyl adipate (7, major) and 7-epitaxol-2'-vinyl adipate (14, minor) (Table 1). Isolated yields of the products (based on the starting amount of taxol) were 60% and 18%, respectively. Thus, thermolysin is an extremely regioselective enzyme toward the 2' hydroxyl moiety of taxol, as no other hydroxyl groups on the taxol molecule were esterified in the enzymatic reaction. In addition to divinyl adipate, several other straight-chain vinyl esters were suitable for the therinolysin-catalyzed acylation of taxol under conditions described above for divinyl adipate. In all cases, acylation was specific to the 2'-hydroxyl group of taxol with 96 h conversions of at least 50% (Table 1).[17,18]

In the second step of the two-step acylation procedure, following purification of the taxol 2'-vinyl adipate by preparative HPLC, hydrolysis of the terminal vinyl ester group was performed in acetonitrile (containing 1% water) catalyzed by the lipase from *Candida antartica* (75 mg/ml) to give taxol 2'-adipic acid (29) with 75% isolated yield. Taxol 2' vinyl adipate was also used as the acyl donor for transesterification in dry acetonitrile containing glucose (0.36 M) as the acyl acceptor resulting in the formation of taxol 2' (adipoyl)glucose (30) with 85% isolated yield (presumably linked selectively to the 6-hydroxyl moiety of the sugar[21]). Using a similar procedure, we also succeeded in synthesizing taxol 2'-(adipoyl)mannose and taxol 2'-(adipoyl)fructose starting from taxol 2'-vinyl adipate and the corresponding sugar. This two-step process demonstrates the unique advantage or enzymatic catalysis, namely the high regloselectivity or hydrolysis/transesterification to generate taxol derivatives.[22]

Both the free adipic acid and sugar-containing taxol derivatives were more soluble in water than taxol itself. Specifically, the solubility of taxol (<4 µg/ml) is increased 58-fold and 1625-fold for the taxol 2'-(adipoyl)glucose and taxol 2'-adipic acid, respectively. Thus, the enzymatic addition of polar functionalities onto the 2'-position of taxol results in dramatic improvement in taxol's water solubility.

TABLE 1

Enzymatically synthesized 2'-acyl taxol derivatives[a]

| Acyl R group in taxol-OR | cmpd | taxol derivative | cmpd | 7-epitaxol derivative[c] |
|---|---|---|---|---|
| Esters | | | | |
| —C(O)CH$_3$ | 1 | 57 | 8 | 30 |
| —C(O)CH$_2$Cl | 2 | 70 | 9 | 3 |
| —C(O)CH=CH$_2$ | 3 | 80 | 10 | 10 |
| —C(O)CH$_2$CH$_3$ | 4 | 78 | 11 | 12 |
| —C(O)(CH$_2$)$_2$CH$_3$ | 5 | 67 | 12 | 11 |
| —C(O)(CH$_2$)$_4$CH$_3$ | 6 | 50 | 13 | 7 |
| —C(O)CH$_2$(CH$_2$)$_4$C(O)OCH=CH$_2$ | 7 | 69 | 14 | 31 |
| Carbonates | | | | |
| —C(O)O(CH$_2$)$_3$CH$_3$ | 15 | 80 | 22 | 20 |
| —C(O)ON=C(CH$_3$)$_2$ | 16 | 89 | 23 | 11 |
| —C(O)OCH$_2$CH=CHCH$_2$OC(O)OCH=CH$_2$ | 17 | 81 | 24 | 10 |
| —C(O)OCH$_2$CH$_2$CH(CH$_3$)OC(O)OCH=CH$_2$ | 18 | 60 | 25 | 9 |
| —C(O)OCH$_2$CH$_2$CH$_2$OC(O)OCH=CH$_2$ | 19 | 69 | 26 | 9 |
| 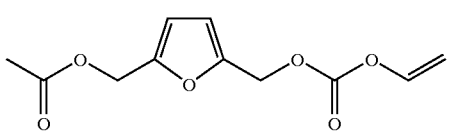 | 20 | 83 | 27 | 13 |
| 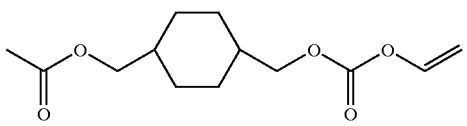 | 21 | 25 | 28 | 4 |

The biocatalysts used in the biocatalytic reactions may be crude or purified enzymes, cellular lysate preparations, partially purified lysate preparations, living cells or intact non-living cells, used in solution, in suspension, or immobilized on magnetic or non-magnetic surfaces.

In addition, non-specific chemical reactions may also be used in conjunction with the biocatalytic reaction to obtain the library of modified starting compounds. Examples of such non-specific chemical reactions include: hydroxylation of aromatics and aliphatics; oxidation reactions; reduction reactions; hydration reactions; dehydration reactions; hydrolysis reactions; acid/based catalyzed esterification; transesterification; aldol condensation; reductive amination; amminolysis; dehydrohalogenation; halogenation; acylation; acyl substitution; aromatic substitution; Grignard synthesis; Friedel-Crafts acylation; etherification.

The biocatalytic reaction can be performed with a biocatalyst immobilized to magnetic particles forming a magnetic biocatalyst. The method of this embodiment is performed by initiating the biocatalytic reaction by combining the immobilized biocatalyst with substrate(s), cofactors(s) and solvent/buffer conditions used for a specific biocatalytic reaction. The magnetic biocatalyst is removed from the biocatalytic reaction mixture to terminate the biocatalytic reaction. This is accomplished by applying an external magnetic field causing the magnetic particles with the immobilized biocatalyst to be attracted to and concentrate at the source of the magnetic field, thus effectively separating the magnetic biocatalyst from the bulk of the biocatalyst reaction mixture. This allows for the transferral of the reaction mixture minus the magnetic biocatalyst from a first reaction vessel to a second reaction vessel, leaving the magnetic biocatalyst in the first reaction vessel. A second biocatalytic reaction is conducted completely independent of the first biocatalytic reaction, by adding a second biocatalyst immobilized to magnetic particles to the second reaction vessel containing the biocatalytic reaction mixture transferred from the first reaction vessel. Finally, these steps are repeated to accomplish a sequential series of distinct and independent biocatalytic reactions, producing a corresponding series of modified starting compounds.

The biocatalytic reactions can also be performed using biocatalysts immobilized on any surface which provides for the convenient addition and removal of biocatalyst from the biocatalytic reaction mixture thus accomplishing a sequential series of distinct and independent biocatalytic reactions producing a series of modified starting compounds.

The biocatalytic reactions can also be used to derivatize known drug compounds producing new derivatives of the drug compound and select individual compounds within this library that exhibit optimal activity.

Also disclosed are specific libraries of organic compounds. Individual libraries are usefull, and have industrial applicability, for screening for new drug candidates, and accordingly, libraries of organic compounds have utility as a tool for drug discovery.

More specifically, a library of derivatives based on 2,3-(methylenedioxy)benzaldehyde is describe in FIG. 1. These compounds have activity as antibiotic and/or antimicrobial compounds, as well as pesticidal and/or anti-fungal activity in the agriculture plant protection field. The enzymes, reagents and solvents used to prepare the nine derivatives are as follows:

Reactions with MDB

| Rxn = (see slide) | Enzyme | Solvent | Reagent |
|---|---|---|---|
| 1 | Mandelonitrile lyase from almond | isopropyl other | acetone cyanohydrin |
| 2 | Saccnaromyces cerevisiae | water | fermentation medium |
| 3 | a. Mandelonitrile lyase from almond | Isopropyl ether | acetone cyanohydrin |
| | b. Lipases from Alcaligenes sp. and Candida lipilytica | n-Hexane 30% tetrahydrofuran | 2-oxo-4-thiazoiidine carboxvlic acid vinyl ester |
| 4 | a. Saccnaromyces cerevisiae | water | fermentation medium |
| | b. Lipases from Alcaiigenes sp. and Candida lipilytica | n-Hexane 30% tetrahydrofuran | 1-amino-4-(2-hydroxyethyl) piperazine divinyl carbonate |
| | c. Lipases from Mucor miehei and Candida antarctica | n-Hexane 30% tetrahydrofuran | l-aziridine ethanol |
| 5 | Aspergillus aiiaceus | water | fermentation medium |
| 6 | Xanthine oxidase | water | oxygen |
| 7 | a. Aspergillus aliaceus | water | fermentation medium |
| | b. β-Galactosidase from E. coli | 50% acetone/water | p-nitrophenyl galactoside |
| | c. Lipases from Mucor miehei and Candida antarctica | acetonitrile | o-chlorobenzoic acic vinyl ester |
| 8 | Aspergillus aiiaceus | water | fermentation medium |
| 9 | a. Aspergillus aiiaceus | water | fermentation medium |
| | b. β-Galactosidase from E. coli | 50% acetone/water | p-nitrophenyl galactoside |

Figure 2:
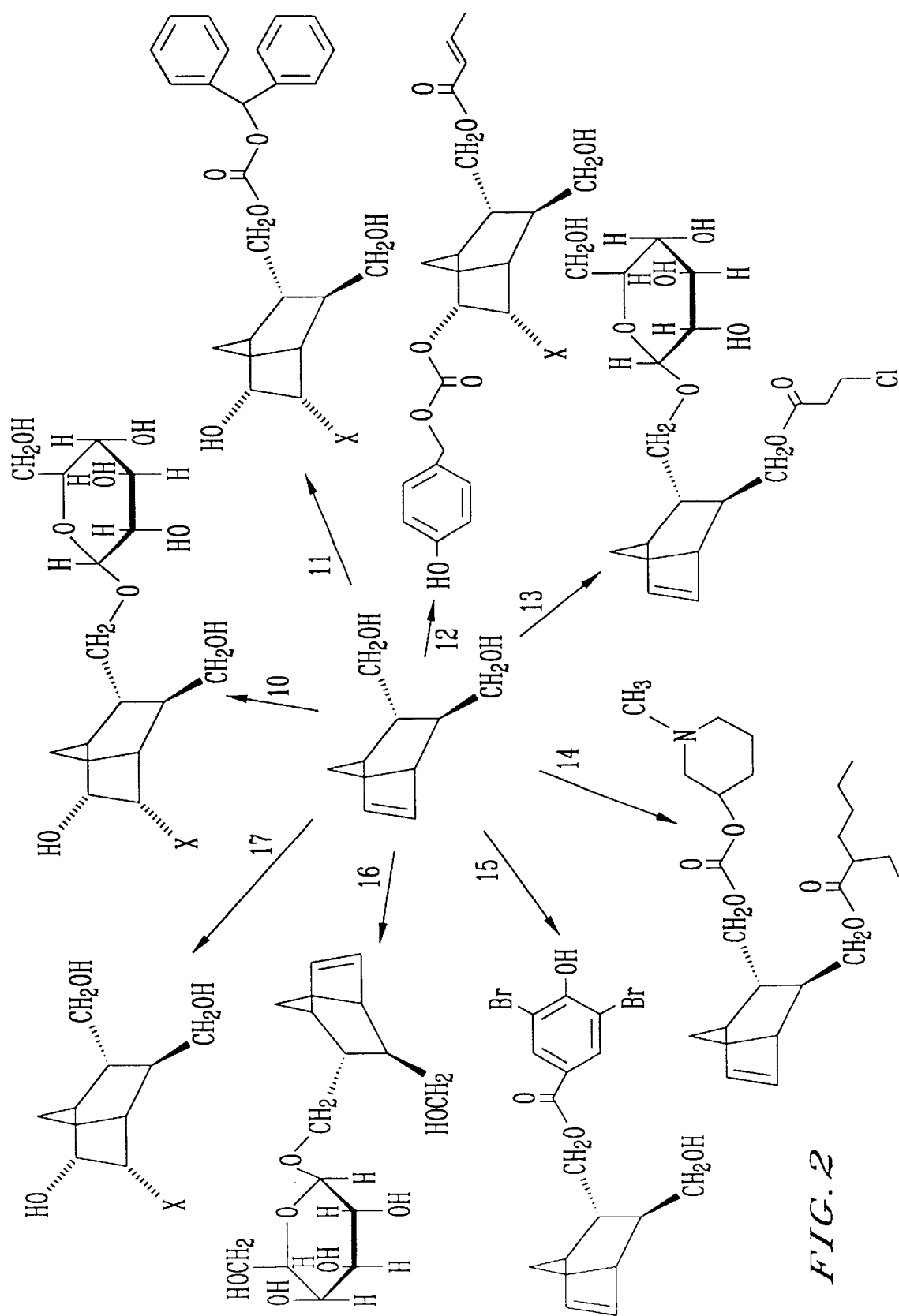
FIG. 2 describes a library of derivatives basedde on (±)-(2-endo,3-exo)-bicyclo[2.2.2]octo-5-ene-2,3-dimethanol.

More specifically, a library of derivatives based on (±)-(2endo,3-exo)-bicyclo[2.2.2]octo-5-ene-2,3-dimethanol is describe in FIG. 2. In FIG. 2, the group X is a halogen atom, preferably chlorine, bromine or iodine, more preferably bromine. These compounds have activity as antibiotic and/or antimicrobial compounds, as well as pesticidal and/or anti-fungal activity in the agriculture plant protection field. The enzymes, reagents and solvents used to prepare the derivatives are as follows:

Reactions with BOD

| | | | |
|---|---|---|---|
| 10 | a. bromoperoxidase from Corallina officinaiis | 30% acetonitrile/water | KBr (or KCl) and $H_2O_2$ |
| | b. α-glucosidase from Bacillus stearothermophilus | 50% acetone/water | p-nitropnenyi glucoside |
| 11 | a. bromoperxidase from Corallina officinaiis | 30% acetonitrile/water | KBr (or KCl) and $H_2O_2$ |
| | b. Lipases from candida rugosa and Pseudomonas cepacia | n-Hexane/30% tetrahydrofuran | 3,3-diphenyl propionic acid vinyl ester |
| 12 | a. bromoperoxidase from Corallina officinaiis | 30% acetonitrile/water | KBr (or KCl) and $H_2O_2$ |
| | b. Lipases from candida rugosa and Pseudomonas cepacia | n-Hexane/30% tetrahydrofuran | crotonic acid vinyl ester and p-hydroxybenzyl alcohol vinyl carbonate |

-continued

Reactions with BOD

| | | | |
|---|---|---|---|
| 13 | a. Lipases from candida rugosa and Pseudomonas cepacia | n-Hexane/30% tetrahydrofuran | chloroacetic acid vinyl ester |
| | b. α-glucosidase from Bacillus stearothermophilus | 50% acetone/water | p-nitrophenyl glucoside |
| 14 | Lipases from Mucor miehei and Candida antarctica | acetonitriie | 2-ethyl hexanoic acid vinyl ester and 1-methyl-3-piperidine methanol vinyl carbonate |
| 15 | Lipases from Mucor miehei and Candida antarctica | acetonitrile | 3,5-dibromo-4-hyroxy benzoic acid vinyl ester |
| 16 | βGalactosidase from E. coli | 50% acetone/water | p-nitrophenyl galactoside |
| 17 | Bromoperoxidase from Corallina officinaiis | 30% acetonitrile/water | KBr (or KCl) and $H_2O_2$ |

Figure 3:
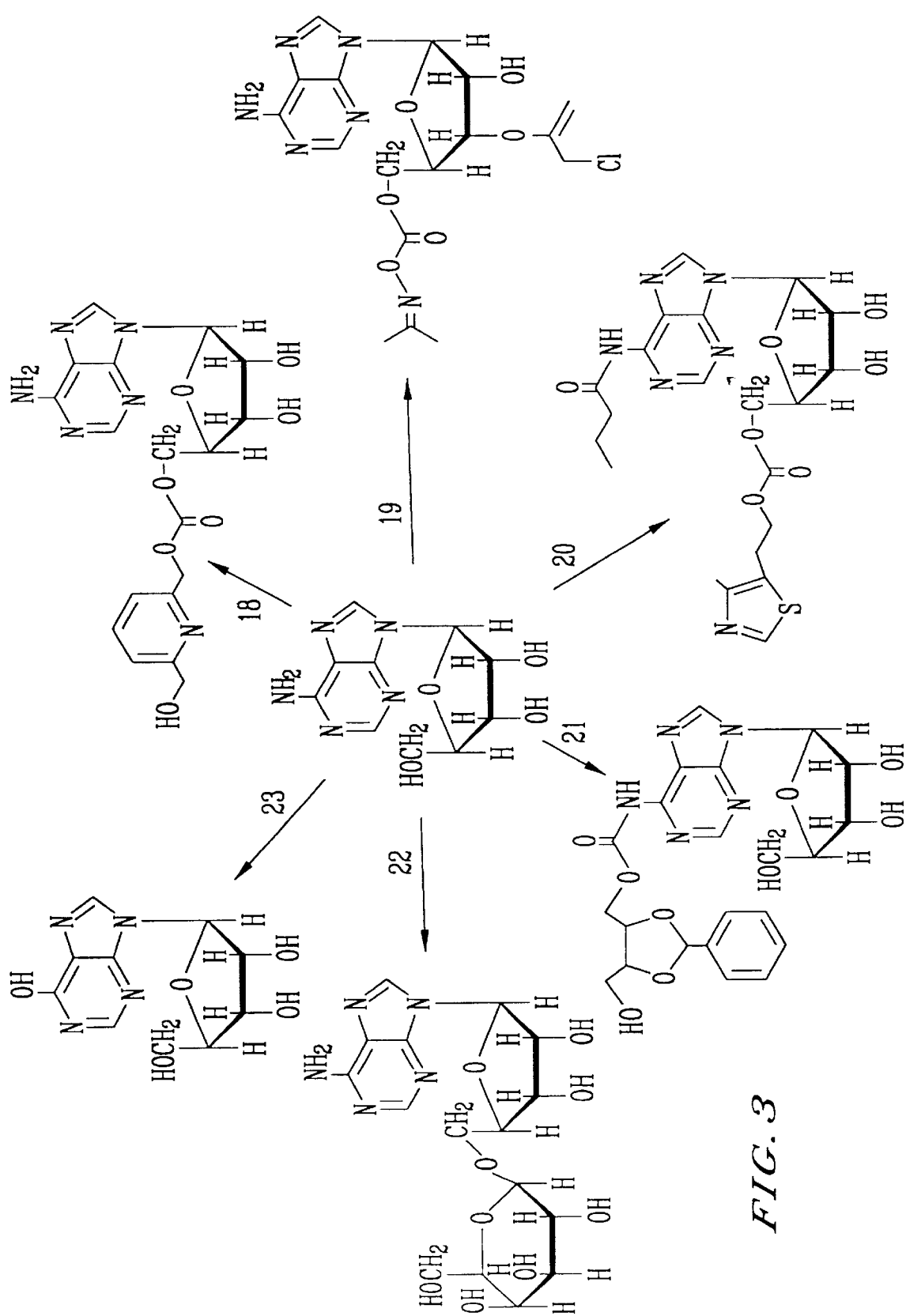
FIG. 3 describes a library of derivatives based on adenosine.
Figure 4A:
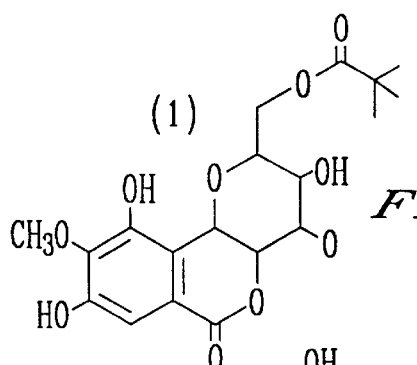
FIG. 4 describes specific bergenin derivatives.
Figure 4B:
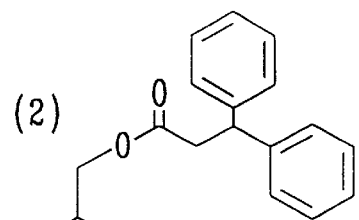
Figure 4C:
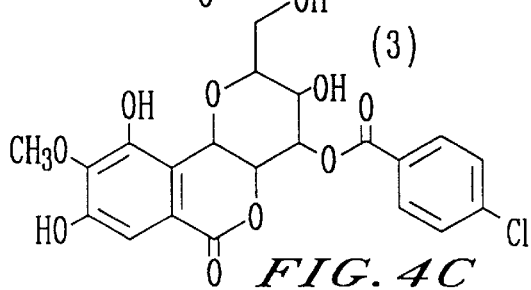
Figure 4D:
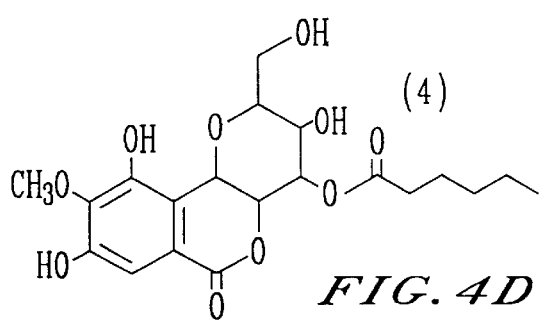
Figure 4E:
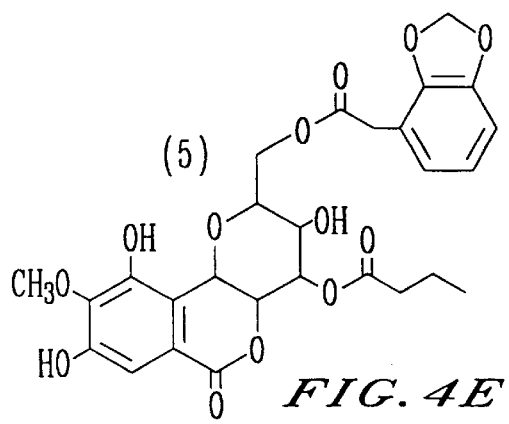
Figure 4F:
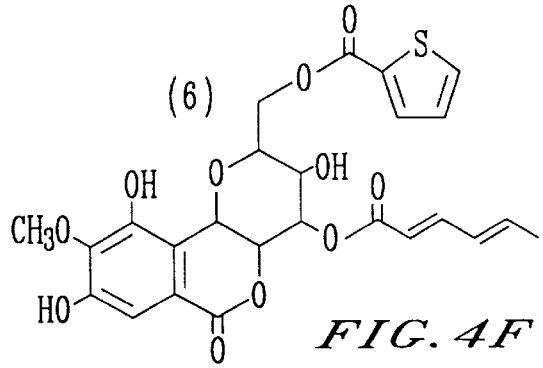
Figure 4G:
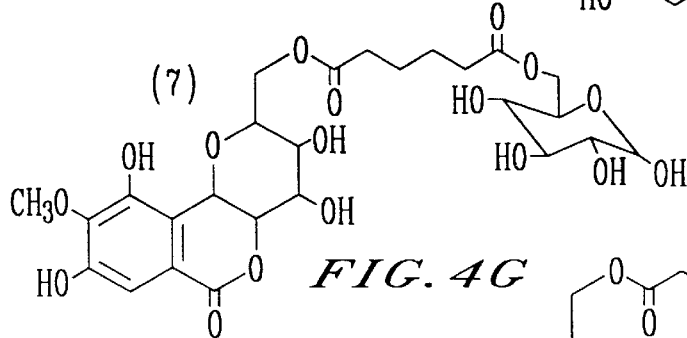
Figure 4H:
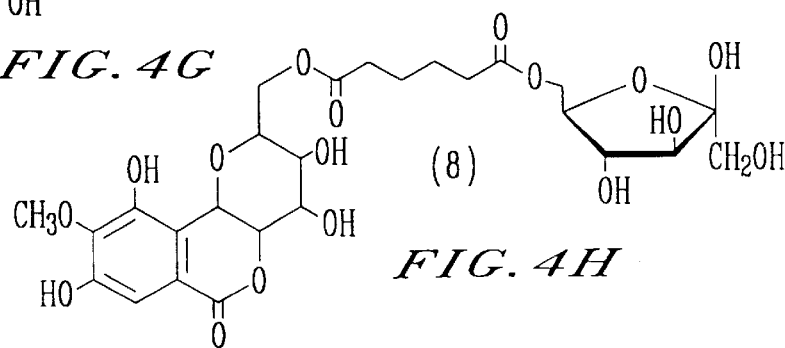
Figure 4I:
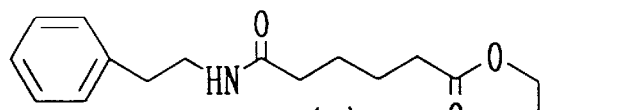
Figure 4I:
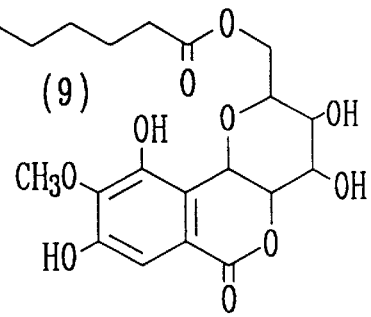
Figure 4J:
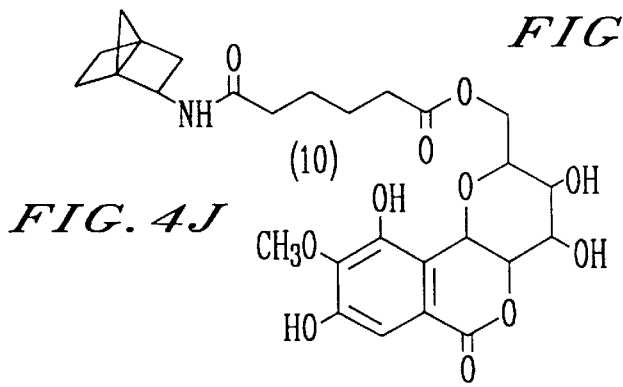
Figure 4K:
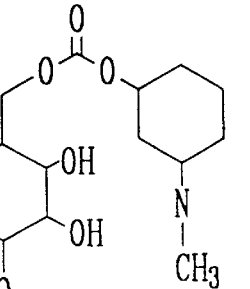
Figure 4L:
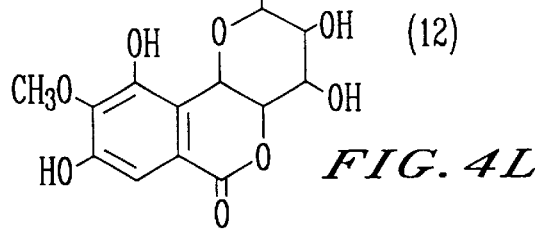
Figure 4M:
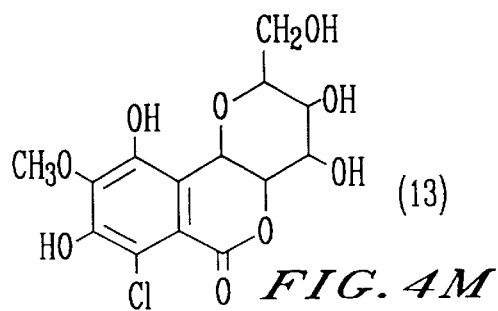
Figure 4N:
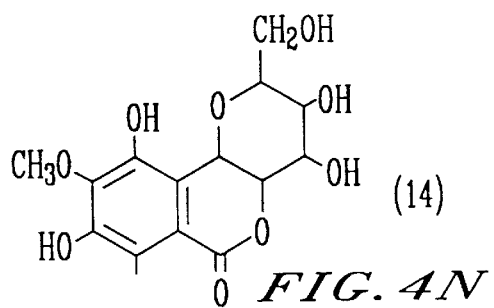
Figure 4O:
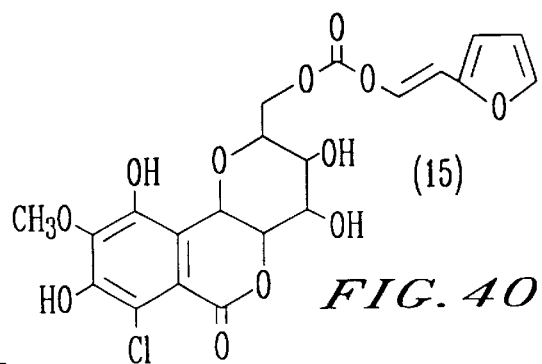
Figure 4P:
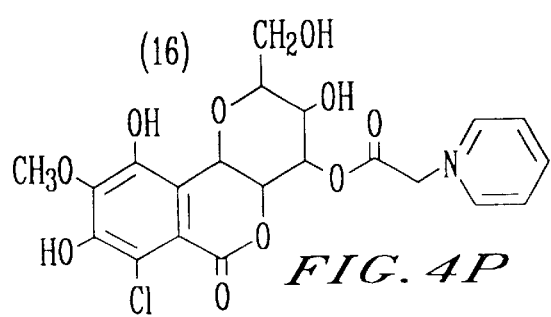

More specifically, a library of derivatives based on adenosine describe in FIG. 3. These compounds have activity in the pharmaceutical area as anti-viral and anti-cancer compounds. The enzymes, reagents and solvents used to prepare the derivatives are as follows:

Reactions with ADS

| | | | |
|---|---|---|---|
| 18 | Lipases from Mucor miehei and Candida antarctica | acetonitrile | 2,6-pyridine dimethanol vinyl carbonate |
| 19 | Lipases from Mucor miehei and Candida antarctica | acetonitrile | acetone oxime vinyl carbonate and chloro acetic acid vinyl ester |
| 20 | a. Acylase from Aspergiilus melleus | acetonitrile | butyric acid vinyl ester |
| | b. Lipases from Mucor miehei and Candida antarctica | acetonitrile | 4-methyl-5-thiazole ethanol vinyl carbonate |
| 21 | Acylase from Aspergiilus melleus | acetonitrile | 2,3-0-benzylidene-L-threitol vinyl carbonate |
| 22 | β-Galactosidas from E. coli | 50% acetone/water | p-nitrophenyl galactoside |
| 23 | Adenosine deaminase from bovine | water | water |

Also disclosed are taxol-2'-adipate derivatives of the formula.

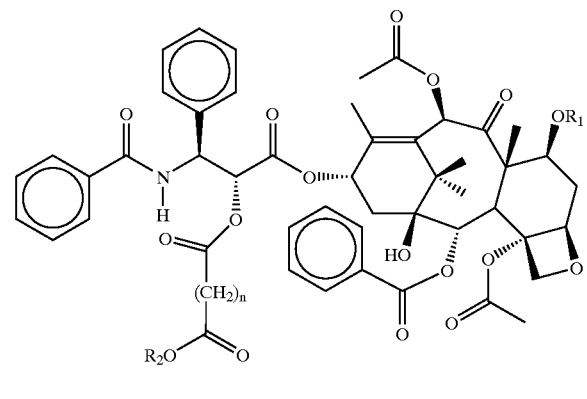

wherein:

R₁ is hydrogen, $C_{1-10}$ alkyl ester, halosubstituted $C_{1-10}$ alkyl ester, or $CO(CH_2)_nCOR_3$ where n is an integer of 2–10 and $R_3$ is hydrogen, $C_{1-10}$ alkyl or $C_{1-10}$ alkenyl;

n is an integer of 2–10; and

R₂ is hydrogen, $C_{1-10}$ alkyl, $C_{1-10}$ alkenyl, or a 6 substituted saccharide compound selected from the group consisting of glucose, galactose, allose, altrose, mannose, gulose, idose, talose, lactose, cellobiose, sucrose, fructose, deoxynojirimycin, N-acetyl glucosamine, N-acetyl galactosamine and maltose.

Examples of suitable $C_{1-10}$ alkyl esters are acetate, acrylate, propionate, butyrate and hexanoate. An example of a suitable halosubstituted $C_{1-10}$ alkyl ester is choloropropionate.

In particular the present invention is directed to the compounds

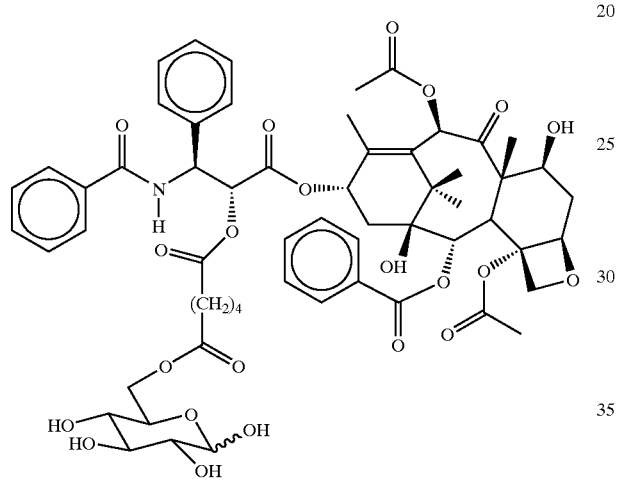

and

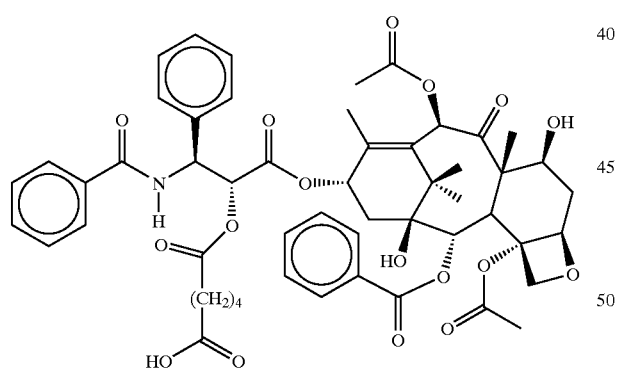

The glucose-6 derivative may be obtained by enzymatic glycosylation of taxol-2'-vinyl adipate with glucose, catalyzed by a lipase from *Candia antarctica*. Taxol-2'-(glucose-6-adipate has a solubility 60 times greater than that of taxol, and has anti-cancer activity analogous to taxol. Taxol-2'adipic acid has a solubility 1,700 tome treater than that of taxol, and has anti-cancer activity analogous to taxol. These compounds have an anti-cancer activity spectrum similar to that of taxol, and the use of these compounds in a method for treating cancer, would be analogous to a method of treating cancer using taxol. Such compounds have industrial applicability as pharmaceutical compounds for treating cancer, as well as in an industrial applicable method of treating cancer.

Also disclosed are derivatives of bergenin, of the formula

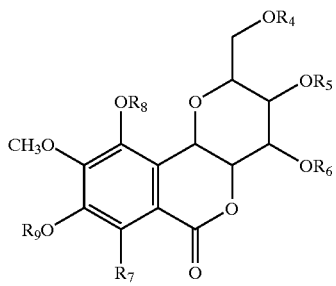

wherein

R₄, R₅, and R₆ are each independently hydrogen, $C_{1-10}$ alkyl ester, $C_{1-10}$ alkyl substituted $C_{1-10}$ alkyl ester, halosubstituted $C_{1-10}$ alkyl ester, $C_{6-20}$ aralkyl ester, halo substituted $C_{6-20}$ aralkyl ester, $C_{6-20}$ aralkenyl ester, a 1 substituted saccharide compound selected from the group consisting of glucose, galactose, allose, altrose, mannose, gulose, idose, talose, lactose, cellobiose, sucrose, fructose and maltose, or $CO(CH_2)_nCOR_{10}$ where n is an integer of 2–10; and R₁₀ is OH, $C_{1-10}$ alkoxy, $C_{1-10}$ alkenyloxy, a 6 substituted saccharide compound selected from the group consisting of glucose, galactose, allose, altrose, mannose, gulose, idose, talose, lactose, cellobiose, sucrose, fructose and maltose, in the open or pyranose form, $NR_{11}R_{12}$ where $R_{11}$ and $R_{12}$ are each independently hydrogen, $C_{1-10}$ alkyl, substitued $C_{1-10}$ alkyl substitued with $C_{1-10}$ alkyl, $C_{6-20}$ aryl or halogen;

R₇ is H, OH, F, Cl, Br, or I;

R₈ and R₉ are each independently hydrogen or $C_{1-10}$ alkyl, provided that when $R_7$ is H, $R_4$, $R_5$ and $R_6$ are not all hydrogen.

These compounds have angeotensin converting enzyme (ACE) inhibiting activity, and are therefor useful in the treatment of hypertension. Examples of suitable $C_{1-10}$ alkyl esters are acetate, acrylate, propionate, butyrate and hexanoate. An example of a suitable halosubstituted $C_{1-10}$ alkyl ester is choloropropionate.

Non-limiting examples of specific groups R₄, R₅ and R₆ are

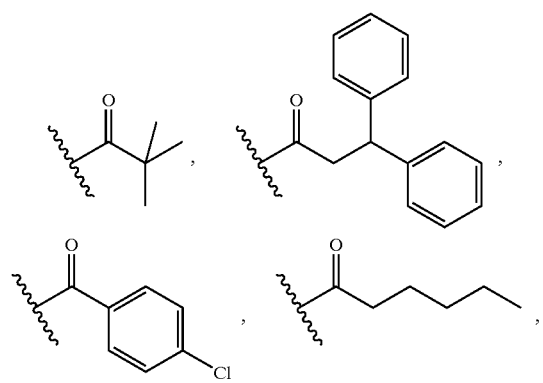

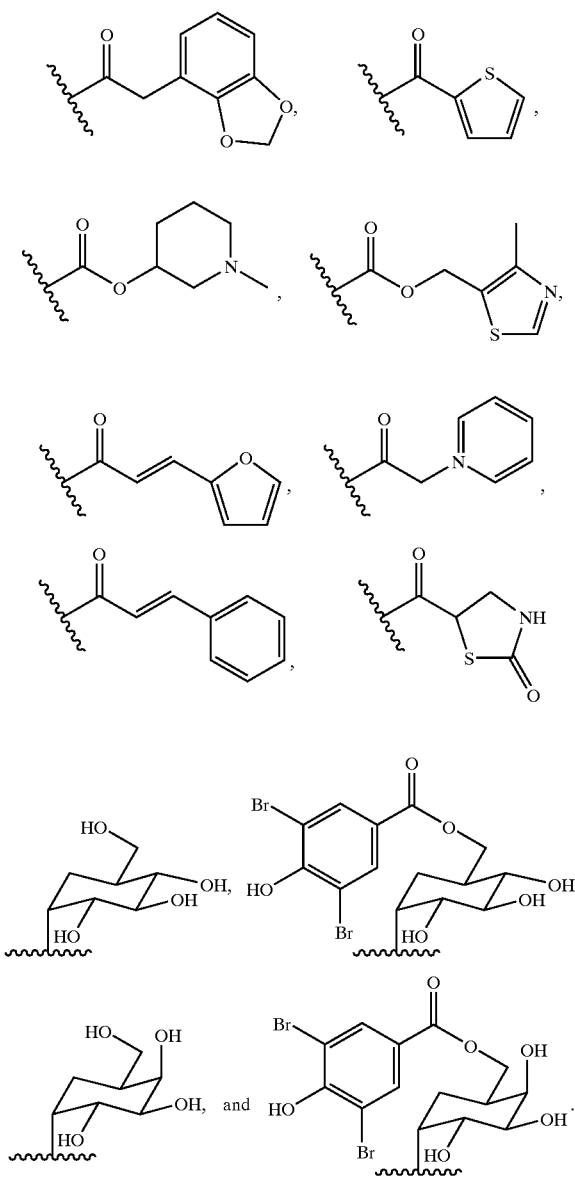

Non-limiting examples of specific groups $R_{10}$ are

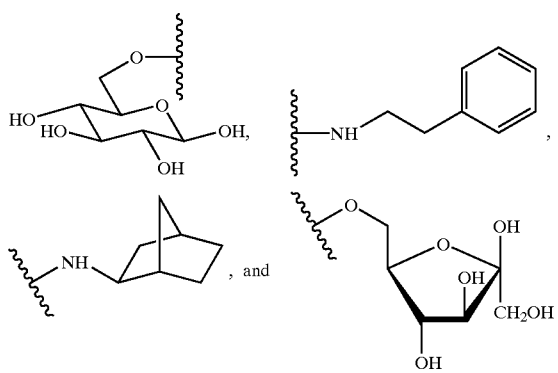

Also described are erythromycin derivatives of the formula

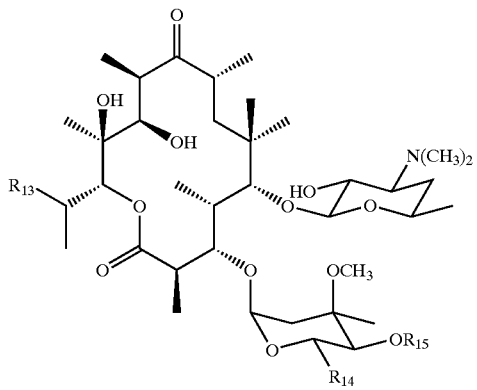

wherein $R_{13}$ is hydrogen or OH;

$R_{14}$ is $CH_3$ or $CO_2H$; and $R_{15}$ is hydrogen or $CO(CH_2)_n COR_{16}$
where n is an integer of 2–10; and $R_{16}$ is OH, $C_{1-10}$ alkoxy, $C_{1-10}$ alkenyloxy, a 6 substituted saccharide compound selected from the group consisting of glucose, galactose, allose, altrose, mannose, gulose, idose, talose, lactose, cellobiose, sucrose, fructose, deoxynojirimycin, N-acetyl glucosamine, N-acetly galactosamine, and maltose, $NR_{17}R_{18}$ where $R_{17}$ and $R_{18}$ are each independently hydrogen, $C_{1-10}$ alkyl, substituted $C_{1-10}$ alkyl substitued with $C_{1-10}$ alkyl, $C_{6-20}$ aryl or halogen;

provided that when $R_{13}$ and $R_{15}$ are each hydrogen, $R_{14}$ is not $CH_3$.

These compounds have antibiotic activity analogous to that of ertythromycin and therefore are usefull as antibiotics.

Also disclosed are taxol-2'-adipate derivatives of the formula.

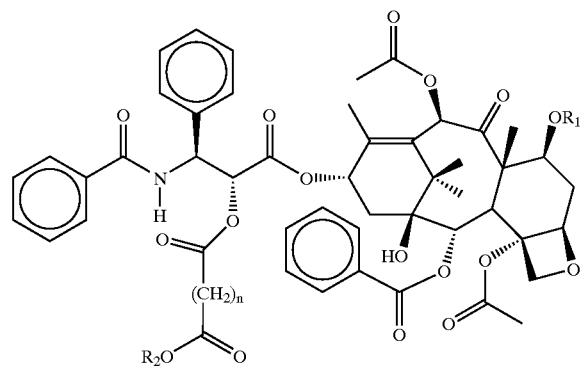

wherein:

$R_1$ is hydrogen, $C_{1-10}$ alkyl ester, halosubstituted $C_{1-10}$ alkyl ester, or $CO(CH_2)_n COR_3$ where n is an integer of 2–10 and $R_3$ is hydrogen, $C_{1-10}$ alkyl or $C_{1-10}$ alkenyl; n is an integer of 2–10; and $R_2$ is hydrogen, $C_{1-10}$ alkyl, $C_{1-10}$ alkenyl, or a 6 substituted saccharide compound selected from the group consisting of glucose, galactose, allose, altrose, mannose, gulose, idose, talose, lactose, cellobiose, sucrose, fructose, deoxynojirimycin, N-acetyl glucosamine, N-acetyl galactosamine, and maltose, wherein when n=4, $R_1$ and $R_2$ are not both hydrogen.

Within the context of the present invention, saccharide groups have been depicted as acylation substituents, in the pyranose form. However, it is within the scope of the present invention for such saccharide groups to exist in an open form or in a furanose form. In addition, within the context of the present invention, all of the described saccharide compounds may be replace by the corresponding aza sugar. The corresponding aza surgar can be prepared by conventional methods known to those of ordinary skill in the art, and then transfered under enzymatic catalysis by a method analogous to that used for the corresponding oxy sugar.

Other features of the invention will become apparent in the course of the following descriptions of exemplary embodiments which are given for illustration of the invention and are not intended to be limiting thereof.

EXAMPLE 1

After testing a wide range of enzymes and solvents[12], thermolysin (an extracellular protease from *Bacillus thermoproteolyticus rokko*) suspended in anhydrous tert-amyl alcohol was identified to be the most effective catalyst for taxol acylation.[13] In particular, this enzyme catalyzed acylation of taxol with a bifunctional acyl donor, divinyl adipate, as determined by TLC and HPLC.[14] The reactivity of thermolysin toward taxol was enhanced ca. 20-fold by lyophilizing the enzyme in the presence of KCl prior to use.[15] Using the salt-activated enzyme preparation (5.7 mg/ml protein), ca. 90% conversion of taxol (14 mM solution) was obtained in 96 h in the presence of 45 mM divinyl adipate. Following termination of the reaction[16], two products were isolated from the reaction mixture via preparative HPLC. The identities of these products were determined by mass spectroscopy and $^1$H-NMR to be taxol 2'-vinyl adipate (7, major) and 7-epitaxol-2'-vinyl adipate (14, minor) (Table 1). Isolated yields of the products (based on the starting amount of taxol) were 60% and 18%, respectively.

In the second step of the two-step acylation procedure, following purification of the taxol 2'-vinyl adipate by preparative HPLC, hydrolysis of the terminal vinyl ester group was performed in acetonitrile (containing 1% water) catalyzed by the lipase from *Candida antartica* (75 mg/ml) to give taxol 2'-adipic acid (29) with 75% isolated yield. Taxol 2' vinyl adipate was also used as the acyl donor for transesterification in dry acetonitrile containing glucose (0.36 M) as the acyl acceptor resulting in the formation of taxol 2' (adipoyl)glucose (30) with 85% isolated yield (presumably linked selectively to the 6-hydroxyl moiety of the sugar[21]). Using a similar procedure, we also succeeded in synthesizing taxol 2'-(adipoyl)mannose and taxol 2'-(adipoyl)fructose starting from taxol 2'-vinyl adipate and the corresponding sugar.

LEGEND TO TABLE 1

[a] Formation of 2'-substituted taxol derivatives was confirmed based on the characteristic downfield shift of the C2' proton signal from 4.7 to 5.6 ppm, representing an unequivocal proof of 2'-substitution.[23] Signals from other taxol ring protons were essentially identical to those previously reported for 2'-acyl taxols.[23b] NMR data for 1: 1.14 (s, 3H, C17-CH$_3$); 1.26 (s, 3H, C16-CH$_3$); 1.68 (s, 3H, C19-CH$_3$); 1.78 (s, 3H, C18-CH$_3$); 1.90 (in, 1H, C6-H); 2.23 (s, 3H, OAc), 2.35 (in, 2H, C14-H); 2.38 (s, 3H, OAc), 2.47 (s, 3H, OAc); 2.55 (in, 1H, C6-H); 3.81 (d, J=6.0, 1H, C3-H); 4.18 (d, J=7.0, 1H, C20-H); 4.32 (d, J=7.0, 1H, C20-H); 4.44 (in, 1H, C7-H); 4.98 (d, J=9.0, 1H, C5-H); 5.51 (d, J=3.0, C2'-H); 5.65 (d, J=7.0, 1H, C2-H); 5.92 (d, J=2.0, 1H, C3'-H); 6.15 (t, J=8.0, 1H, C13-H); 6.27 (s, 1H, C10-H); 6.98 (d, J=8.0, 1H, NH); 7.35 (m), 7.42 (m) and 7.48 (m) (5H, C3'-Ph); 7.40 (m), 7.49 and 7.75 (m) (5H, NC(O)Ph); 7.53 (m), 7.65(m) and 8.14 (m) (5H,C20-COPh).

[b] Determined from relative peak areas on HPLC chromatograms. For structural confirmation, part of the reaction mixture was subjected to preparative HPLC to isolate a small amount of the product needed for mass spectral and NMR analysis.

[c] Formation of 7-epitaxol was found to be a spontaneous process not related to enzyme action. Epimerization occurred during prolonged incubation of taxol in tert-amyl alcohol at the increased temperature required for enzymatic acylation (35° C.). Spontaneous epimerization of taxol in mildly basic aqueous solutions has been observed previously.[24] Epimerization at the 7 position was established based on characteristic merging of signals from protons at C20 into a singlet at 4.3 ppm, and the sift of the C7 proton signal from 4.4 ppm to 3.7 ppm, which unambiguously indicate the formation of 7-epimer.[25] NMR data for 8: 1.15 (s, 3H, C16-CH$_3$); 1.20 (s, 3H, C17-CH$_3$); 1.67 (s, 3 H, C19-CH$_3$); 1.90 (s, 3H, C18-CH$_3$); 2.14 (s, 3H, OAc), 2.18 (s, 3H, OAc), 2.32 (in, 1H, C6-H); 2.37 (in, 2H, C14-H); 2.53 (s, 3H, OAc), 3.67 (br.s., 1H, C7-H); 3.92(d, J=7, 1H, C3-H); 4.38 (s, 2H, C20-H); 4.90 (d, J=8, 1H, C5-H); 5.53 (d, J=3, 1H, C2'-H); 5.75 (d, J=7, 1H, C2-H); 6.0 (dd, J=2.8, 1H, C3'-H); 6.21 (t, 1H, J=8, C13-H); 6.82 (s, 1H, C10-H); 6.90 (d, J=9, 1H, NH); 7.33–8.13 (15H)-Aromatic

LEGEND TO FIG. 1

Two-step enzymatic modification of taxol resulting in taxol 2'-adipic acid (29) and taxol 2'-(adipoyl)glucose (30). Reaction conditions are described in the text.

Taxol 2'-acrylate (3)

1.14 (s, 3H, C17-CH$_3$); 1.22 (s, 3H, C16-CH$_3$); 1.68 (s, 3H, C19-CH$_3$); 1.88 (m, 1H, C6-H); 1.94 (s, 3H, C18-CH$_3$); 2.28 (s, 3H, OAc), 2.35 (m, 2H, C14-H); 2.48 (s, 3H, OAc); 2.54 (m, 1H, C6-H); 3.80 (d, J=6.0, 1H, C3-H); 4.20 (d, J=7.0, 1H, C20-H); 4.38 (d, J=7.0, 1H, C20-H); 4.48 (m, 1H, C7-H); 4.97 (m, 1H, C5-H); 5.50 (d, J=3.0, C2'-H); 5.67 (d, J=7.0, 1H, C2-H); 5.94 (d, J=2.0, 1H, C3'-H); 5.96 (d, J=1,1H, CH$_2$=C); 6.20 (m, 1H, =CHO); 6.24 (t, J=8.0, 1H, C13-H); 6.30 (s, 1H, C10-H); 6.45 (d, J=1, 1H, =CH$_2$); 6.90 (d, J=8.0, 1H, NH);7.30–8.15 (15H,)-Aromatic Taxol 2'-propionate (4)

1.12 (t, 3H, J=8, CH$_3$prop); 1.14 (s, 3H, C17-CH$_3$); 1.22 (s, 3H, C16-CH$_3$);); 1.68 (s, 3H, C19-CH$_3$); 1.84 (m, 1H, C6-H); 1.90 (s, 3H, C18-CH$_3$); 2.20 (m, 2H, CH$_2$, prop); 2.24 (s, 3H, OAc), 2.36 (m, 2H, C14-H); 2.48 (s, 3H, OAc), 2.55 (m, 1H, C6-H); 3.80 (d, J=6.0, 1H, C3-H); 4.18 (d, J=7, 1H, C20-H); 4.31 (d, 1H, J=7, C20-H); 4.44 (m, 1H, C7-H); 4.90 (d, 1H, J=8, C5-H); 5.51 (d, J=3, C2'-H); 5.60 (d, J=7.0 1H, C2-H); 6.00 (dd, J=1.8, 1H, C3'-H); 6.26 (t, J=8.0, 1H, C13-H); 6.29 (s, 1H, C10-H); 6.92 (d, J=8, 1H, NH); 7.13–8.15 (15H)-Aromatic Taxol 2'-butyrate (5)

0.9 (t, 3H, J=8, CH$_3$ but.); 1.14 (s, 3H, C17-CH$_3$); 1.21 (s, 3H, C16-CH$_3$);); 1.62 (m, 2H, CH$_2$, but.); 1.69 (s, 3H, C19-CH$_3$); 1.88 (m, 1H, C6-H); 1.94 (s, 3H, C18-CH 3); 2.24 (s, 3H, OAc), 2.28 (m, 2H, CH$_2$ but. ); 2.36 (m, 2H, C14-H); 2.45 (s, 3H, OAc), 2.54 (m, 1H, C6-H); 3.81 (d, J=6.0, 1H, C3-H); 4.18 (d, J=7, 1H, C20-H); 4.32 (d, 1H, J=7, C20-H); 4.40 (m, 1H, C7-H); 4.90 (d, 1H, J=8, C5-H); 5.51 (d, J=3, C2'-H); 5.65 (d, J=7.0 1H, C2-H); 6.00 (dd, J=1.8, 1H, C3'-H); 6.22 (t, J=8.0, 1H, C13-H); 6.29 (s, 1H, C10-H); 6.85 (d, J=8, 1H, NH); 7.13–8.15 (15H)-Aromatic Taxol 2'-hexanoate (6)

0.8 (t, 3H, J=8, CH₃hex.) ; 1.14 (s, 3H, C17-CH₃); 1.21 (s, 3H, C16-CH₃);); 1.30 (m, 2H, CH₂, hex.); 1.40 (m, 4H, CH₂, hex.); 1.68 (s, 3H, C19-CH₃); 1.88 (m, 1H, C6-H); 1.94 (s, 3H, C18-CH,); 2.24 (s, 3H, OAc), 2.28 (m, 2H, CH₂ hex.); 2.36 (m, 2H, C14-H); 2.45 (s, 3H, OAc), 2.54 (m, 1H, C6-H); 3.80 (d, J=6.0, 1H, C3-H); 4.20 (d, J=7, C20-H); 4.38 (d, 1H, J=7, C20-H); 4.40 (m, 1H, C7-H); 490 (d, 1H, J=8, C5-H); 5.51 (d, J=3, C2'-H); 5.65 (d, J=7.0 1H, C2-H); 6.00 (m, 1H, C3'-H); 6.22 (t, J=8.0, 1H, C13-H); 6.30 (s, 1H, C10-H); 6.85 (d, J=8, 1H, NH); 7.30–8.15 (15H)-Aromatic Taxol 2'-vinyl adipate (7)

1.14 (s, 3H, C17-CH₃); 1.26 (s, 3H, C16-CH₃); 1.38 (m, 4H, adip); 1.54 (m, 2H, adip); 1.68 (s, 3H, C18-CH₃); 1.88 (m, 1H, C6-H); 1.95 (s, 3H, C19-CH₃); 2.23 (s, 3H, OAc), 2.25 (m, 2H, adip 2.35 (m, 2H, C14-H); 2.47 (s, 3H, OAc); 2.55 (m, 1H, C6-H); 3.81 (d, J=6, 1H, C3-H); 4.18 (d, J=7, 1H, C20-H); 4.32 (d, J=7.0, 1H, C20-H); 4.44 (m, 1H, C7-H); 4.55 (dd, J=7.1, 1H) and 4.88 (dd, J=9.1, 1H, CH₂=C); 4.98 (d, J=9.0, 1H, C5-H); 5.50 (d, J=3.0, 1H, C2'-H); 5.67 (d, J=7.0, 1H, C2-H); 5.95 (m, 1H, C3'H); 6.25 (t, J=8.0, 1H, C13-H); 6.31 (s, 1H, C10-H); 7.0 (d, J=8.0, 1=H, NH); 7.21 (m, 1H, HC=C); 7.35 (m), 7.42 (m) and 7.48 (m) (5H, C3'-Ph); 7.40 (m), 7.49 and 7.75 (m), (5H, NC(O)Ph); 7.53 (m), 7.62 (m) and 8.13 (m) (5H, C20-COPh)

7-epi-Taxol 2'-acrylate (10)

1.14 (s, 3H, C16-CH₃); 1.20 (s, 3H, C17-CH₃); 1.70 (s, 3H, C19-CH₃); 1.90 (s, 3H, C18-CH₃); 2.20 (s, 3H, OAc), 2.32 (m, 1H, C6-H); 2.37 (m, 2H, C14-H); 2.50 (s, 3H, OAc), 3.67 (br.s., 1H, C7-H); 3.90(m, 1H, C3-H); 4.38 (s, 2H, C20-H); 4.90 (d, J=8, 1H, C5-H); 5.61 (d, J=2, 1H, C2'-H); 5.75 (d, J=7, 1H, C2-H); 5.96 (d, J=I, 2H, =CH₂ overlap with C3'-H); 6.0 (m, 1H, C3'-H); 6.2 (m, 1H, =CHO, overlap with C13-H) 22 (t, 1H, J=8, C13-H); 6.45 (d, J=1, 1H, =CH₂); 6.82 (s, 1H, C10-H); 6.90 (d, J=9, 1H, NH); 7.33–8.13 (15H)-Aromatic 7-epi-Taxol 2'-propionate (11)

1.11 (t, J=8, 3H, CH₃ prop); 1.14 (s, 3H, C16-CH₃); 1.18 (s, 3H, C17-CH₃); 1.68 (s, 3H, C19-CH₃); 1.90 (s, 3H, C18-CH₃); 2.21 (m, 2H, CH₂ prop.); 2.24 (s, 3H, OAc), 2.32 (m, 1H, C6-H); 2.37 (m, 2H, C14-H); 2.54 (s, 3H, OAc), 3.70 (br.s., 1H, C7-H); 3.93(d, J=7, 1H, C3-H); 4.49 (s, 2H, C20-H); 4.94 (d, J=8, 1H, C5-H); 5.56 (d, J=3, 1H, C2'-H); 5.76 (d, J=7, 1H, C2-H); 6.0 (m, 1H, C3'-H); 6.23 (t, 1H, J=8, C13-H); 6.82 (s, 1H, C10-H); 6.90 (d, J=9, 1H, NH); 7.33–8.13 (15H)-Aromatic 7-epi-Taxol 2'-butyrate (12)

0.90 (t, J=8, 3H, CH₃ but); 1.14 (s, 3H, C16-CH₃); 1.18 (s, 3H, C17-CH₃); 1.62 (m, 2H, CH₂but.); 1.67 (s, 3H, C19-CH₃); 1.91 (s, 3H, C18-CH₃); 2.18 (s, 3H, OAc), 2.28 (m, 2H, CH₂ but.); 2.33 (m, 1H, C6-H); 2.37 (m, 2H, C14-H); 2.52 (s, 3H, OAc), 3.70 (br.s., 1H, C7-H); 3.90 (d, J=7, 1H, C3-H); 4.40 (s, 2H, C20-H); 4.94 (d, J=8, 1H, C5H); 5.56 (d, J=3, 1H, C2'-H); 5.75 (d, J=8, 1H, C2-H); 6.0 (m, 1H, C3'-H); 6.22 (t, 1H, J=8, C13-H); 6.83 (s, 1H, C10-H); 6.90 (d, J=9, 1H, NH); 7.34–8.13 (15H)-Aromatic 7-epi-Taxol 2'-vinyl adipate (14)

1.14 (s, 3H, C16-CH₃); 1.20 (s, 3H, C17-CH₃); 1.40 (m, 4H, adip); 1.58 (m, 2H, adip); 1.70 (s, 3H, C19-CH₃); 1.88 (s, 3H, C18-CH₃); 2.21 (s, 3H, OAc), 2.24 (m, 2H, adip.); 2.32 (m, 1H, C6-H); 2.35 (m, 2H, C14-H); 2.49 (s, 3H, OAc), 3.65 (br.s., 1H, C7-H); 3.92(d, J=7, 1H, C3-H); 4.37 (s, 2H, C20-H); 4.52 (m, 1H, =CH₂); 4.83 (d, J=8, 1H, =CH₂); 4.93 (m, 1H, C5-H); 5.53 (d, J=3, 1H, C2'-H); 5.73 (d, J=7, 1H, C2H); 6.0 (dd, J=1.10, 1H, C3'-H); 6.22 (t, 1H, J=8, C13-H); 6.81 (s, 1H, C10-H); 7.02 (d J=11, 1H, NH); 7.10 (m, 1H, =CHO); 7.33–8.13 (15H)-Aromatic Taxol 2'-butylcarbonate (15)

0.95 (t, 3H, J=8, CH₃ but.); 1.14 (s, 3H, C17-CH₃); 1.24 (s, 3H, C16-CH₃); 1.46 (m, 4H, CH₂, but.); 1.69 (s, 3H, C19-CH₃); 1.88 (m, 1H, C6-H); 1.93 (s, 3H, C18-CH₃); 2.23 (s, 3H, OAc), 2.36 (m, 2H, C14-H); 2.46 (s, 3H, OAc), 2.54 (m, 1H, C6-H); 3.80 (d, J=7, 1H, C3-H); 4.12 (m, 2H, CH₂but); 4.19 (d, J=7, 1H, C20-H); 4.32 (d, 1H, J=7, C20-H); 4.44 (m, 1H, C7-H); 4.97 (d, 1H, J=8, C5-H); 5.42 (d, J=3, C2'-H); 5.69 (d, J=7.0 1H, C2-H); 6.98 (dd, J=1.8, 1H, C3'-H); 6.22 (t, J=8.0, 1H, C13-H, overlap with C10-H); 6.23 (s, 1H, C10-H, overlap with C13-H); 6.90 (d, J=8, 1H, NH); 7.13–8.15 (15H)-Aromatic Taxol 2'-adipic acid (29)

1.14 (s, 3H, C17-CH₃); 1.26 (s, 3H, C16-CH₃); 1.38 (m, 4H, adip); 1.54 (m, 2H, adip); 1.68 (s, 3H, C19-CH₃); 1.78 (s, 3H, C18-CH₃); 1.88 (m, 1H, C6-H); 2.23 (s, 3H, OAc), 2.24 (m, 2H, adip.); 2.37 (m, 2H, C14-H); 2.38 (s, 3H, OAc), 2.55 (m, 1H, C6-H); 3.80 (d, J=6.0, 1H, C3-H); 4.19 (d, J=7, 1H, C20-H); 4.32 (d, 1H, J=7, C20-H); 4.44 (m, 1H, C7- H); 4.98 (d, 1H; J=8, C5-H); 5.52 (d, J=3, C2'-H); 5.65 (d, J=7.0 1H, C2-H); 5.92 (dd, J1.8, 1H, C3'-H); 6.15 (t , J=8.0, 1H, C13-H); 6.30 (s, 1H, C10-H); 6.98 (d, J=8, 1H, NH); 7.13–8.13 (15H)-Aromatic Taxol 2'-(adipoyl) glucose (30)

1.14 (s, 3H, C17-CH₃); 1.22 (s, 3H, C16-CH₃); 1.38 (m, 4H, adip); 1.54 (m, 2H, adip); 1.68 (s, 3H, C19-CH₃); 1.88 (m, 1H, C6-H); 1.94 (s, 3H, C18-CH₃); 2.28 (s, 3H, OAc), 2.24 (m, 2H, adip.); 2.37 (m, 2H, C14-H); 2.48 (s, 3H, OAc), 2.54 m, 1H, C6H); 4.19 (d, J=7, 1H, C20-H); 3.80 (d, J=6.0, 1H, C3-H); 4.32 (d, 1H, J=7, C20-H); 4.44 (m, 1H, C7-H); 4.97 (m, 1H, C5-H); 5.50 (d, J=3, C2'-H); 5.67 (d, J=7.0 1H, C2H); 5.96 (dd, J=1.8, 1H, C3'-H); 6.23 (t, J=8.0, 1H, C13-H); 6.30 (s, 1H, C10-H); 6.90 (d, J=8, 1H, NH); 7.13–8.13 (15H)-Aromatic; 3.0–3.7 m, 4.6–4.8 m, 5.0–5.2 m.-glucose.

Mass Spectral Data for Acylated Taxol Derivatives

Fast atom bombardment (FAB) mass spectra were obtained on a VG Analytical ZAB-HF mass spectrometer. Samples were bombarded with 8 keV Xe atoms at an atom gun current of 1.5 mA using thioglycerol as the FAB matrix.

| Compound | (M + H) | (M + Na) | Formula Weight Calculated |
|---|---|---|---|
| Taxol 2'-acetate (1) | 896 | 918 | 896 |
| Taxol 2'-acrylate (3) | 908 | 930 | 908 |
| Taxol 2'-propionate (4) | 910 | 932 | 910 |
| Taxol 2'-butyrate (5) | 924 | 946 | 924 |
| Taxol 2'-hexanoate (6) | 952 | 974 | 952 |
| Taxol 2'-butylcarbonate (15) | 955 | 992* | 954 |
| Taxol 2'-adipate (29) | 982 | 1005 | 982 |
| Taxol 2'-(adipoly) glucose (30) | — | 1166 | 1143 |

*(M + Na + NH³⁾ +

Figure 5:
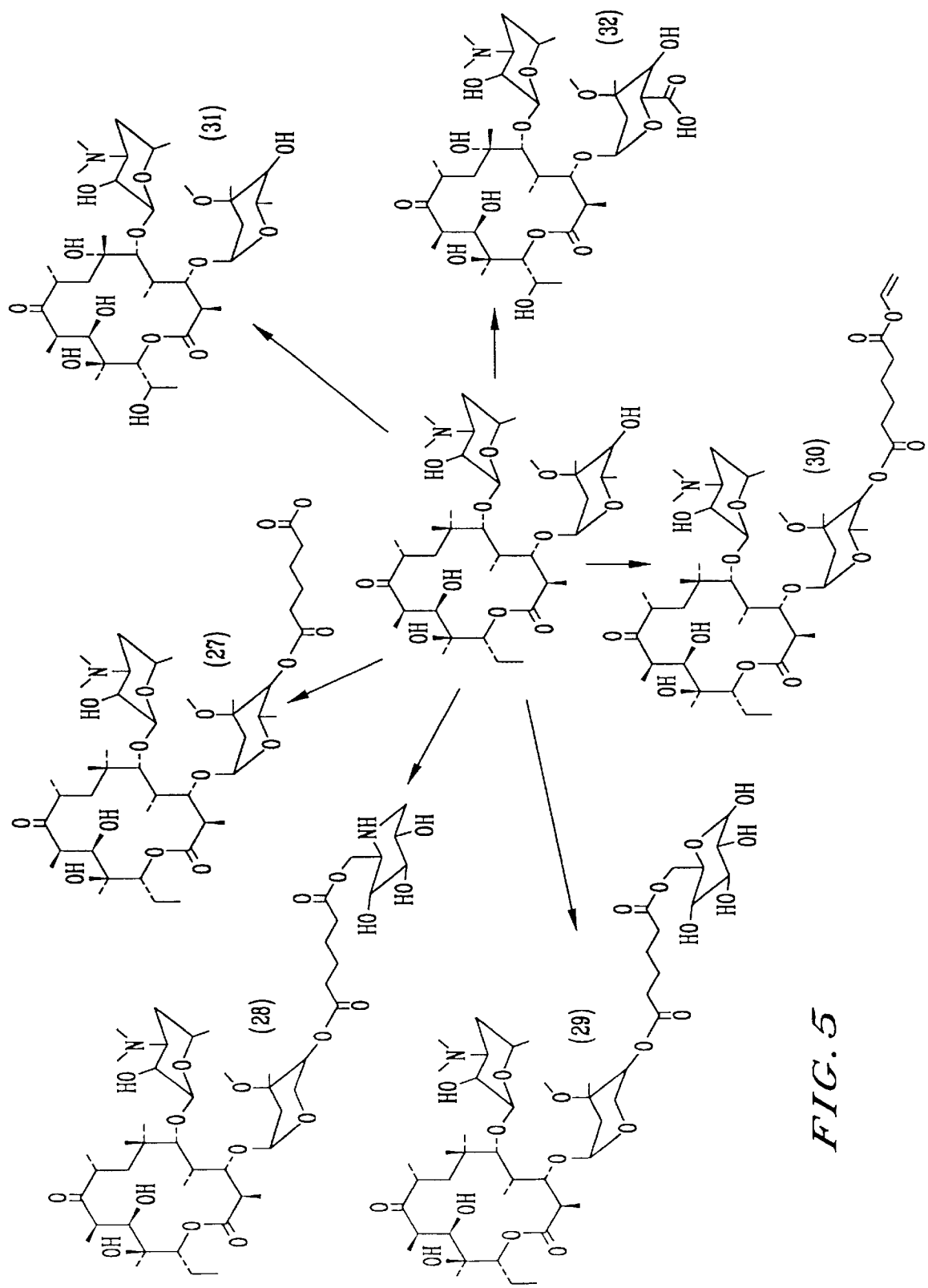
FIG. 5 describes specific erythromycin derivatives.

During the course of Examples 2–5, compound numbers are used which refer to the compound numbers appering in FIGS. 4 and 5

EXAMPLE 2

Compounds 1, 2, 5, 6, 7, 8, 9, 10, 11, 12, 15, 16, 20, 22, 23, 24, 25

Transesterification at primary hydroxyl group of bergenin or other bergenin products using various acyl donors (vinyl ester, vinyl carbonates, trifluoroethyl esters) To a mixture of lipases from *Pseudomonas cepacia* and *Rhizopus oryzae*

(immobilized on Accurel), *Mucor miehei* and *Candida antarctica* (200 mg/ml total enzyme) and molecular sieves, add a suspension containing 20 mM bergenin and 22 mM ester in dry acetonitrile. Incubate at 45° C. with 250 rpm shaking for 6 days.

Compounds 3, 4, 5, 6, 16, 24

Transesterification at secondary hydroxyl group of bergenin or other bergenin products using various acyl donors To subtilisin Carlsberg (40 mg/ml total enzyme), add a solution of 20 mM bergenin and 40 mM ester in toluene with 5% DMSO. Incubate at 45° C. with 250 rpm shaking for 6 days.

Compounds 7, 8, 9, 10

Transesterification of bergenin with amines, sugars and alcohols using bergenin vinyl adipate as acyl donor To a mixture of lipases from *Pseudomonas cepacia*, from Pseudomonas sp., and porcine pancreatic lipase, all immobilized on Accurel, and molecular sieves, add a 20 mM solution or suspension of bergenin vinyl adipate and 40 mM of corresponding amine, alcohol or sugar in dry acetonitrile. Incubate at 45° C. with 250 rpm shaking for 3 days.

Compounds 17,18

Glycosylation of Bergenin

To a mixture of 25 mM bergenin, 40 mM potassium phosphate buffer at pH 6, 25 mM pnitrophenol donor in 25% acetonitrile and 75% water add 3 units per milliliter enzyme (α-galactosidase from green coffee beans, or α-glucosidase from *Bacillus stearothermophilis*). Incubate at 30° C. for 4 h in the case of α-glucosidase or 2 days in the case of α-galactosidase. The reaction is stopped by boiling for 15 minutes.

EXAMPLE 3

Compounds 28, 29

Acylation of Deoxynojirimycin and Glucose using Erythromycin Vinyl Adipate as Acyl Donor To a mixture of 5 mM erythromycin vinyl adipate and 20 mM sugar in acetonitrile add 10 mg/ml *Candida antarctica* lipase and 10 mg/ml lipase from Pseudomonas sp. In the case of deoxynojirimycin-HCI the reaction mixture contains 40 mM triethyl amine. incubate at 45° C. with 250 rpm shaking for 14 days over molecular sieves.

Compounds 27, 30

Acylation of Erythromycin using Divinyl Adipate (27) and Synthesis of Acidic Derivative (30)

To a mixture of lipases (2 mg/ml each) from *Humicola lanuginosa, Rhizopus arrhizius, porcine pancreas,* Pseudomonas sp., Rhizopusjavanicus, and *Candida lipolytica*, 50 mM erythromycin in 90% acetonitrile and 10% DMSO add 1 M divinyl adipate. Incubate at 45° C. with 250 rpm shaking for 14 days. The corresponding acid is formed by incubating the product of the above reaction (compound 27, 5 mM) with lipase from *Candida antarctica* (10 mg/ml) in acetonitrile containing 1% water at 30° C. with 250 rpm shaking for 24 h.

EXAMPLE 4

Compounds 13,15,16,19,26

Halogenation of Bergenin and its Derivatives using Chloroperoxidase

To a solution of 6 mM bergenin, 6 mM KCl, and 0.8 mg/ml chloroperoxidase from *Caldariomyces fumago* in 0.1 M phosphate buffer pH 2.8 add aqueous solution of hydrogen peroxide (0.2 M) to the final concentration of 9 mM over 1.5 h. Incubate the reaction mixture for 2.5 h at room temperature.

Compound 14

Halogenation of Bergenin and its Derivatives using Bromoperoxidase

To a solution of 6 mM bergenin, 12 mM KI, and 1.1 mg/ml bromoperoxidase from *Corallina officinalis* in 0.1 M phosphate buffer pH 6.0 add aqueous solution of hydrogen peroxide to the final concentration of 9 mM. Incubate the reaction mixture for 3 h at room temperature.

EXAMPLE 5

Compound 21–24,31,32

Microbial Hydroxylations of Bergenin and Erythromycin

Microbial cultures used were maintained on Sabouraud-maltose agar slants stored at 4° C. All incubations with growing cells were performed in a soybean meal-glucose medium of the following composition (all per liter): 5 g soybean meal; 20 g glucose; 5 g yeast extract; 5 g NaCl; 5 g K2HPO4; adjusted to pH 6.8 using 6N HCl. The medium was sterilized at 121° C. for 15 minutes.

Fermentations were conducted on an Innova 5000 gyratory shaker (New Brunswick Scientific) at 200–250 rpm and 30° C. Delong flasks were filled to one-fifth their total volume with media for the incubations.

Fermentations were initiated by adding the surface growth from one slant into 25 ml of medium and incubating for 48 hrs. The 48-hour "stage I" growth was used to inoculate a fresh "stage II" flask. The inoculum volume was 10% of the volume of Stage II media. Genistein, 5,6-benzoflavone, 20-methylcholanthrene, or nothing (depending on the microorganism) was also added to stage II cultures to a final concentration of 1–100 $\mu$M. After 24–48 hrs of Stage II growth, depending on the microorganism, a 50 mg/ml stock of the parent compound was added to the Stage II fermentation to a final concentration of 1 mg/ml. Samples were taken from the fermentation at several points over the next 150 hrs, and the reaction was stopped by centrifugation at 13,000 rpm for 10 minutes and extracting the fermentation broth with an equal amount of ethyl acetate 3 times, drying the the pooled ethyl acetate over $Na_2SO_4$, and rotory evaporating to remove solvent.

This applcation is based on U.S. Provisional applicaiton No. 60/003,661 file in the U.S. Patent Office on Aug. 11, 1995 the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

1. For reviews on taxol see: (a) Kingston, D. G. I. *Trends Biotechnol.* 1994, 12, 222. (b) Rowinsky, E. K.; Onerto, N.; Canetta, R. M.; Arbuck, S. G. ; *Sem. Oncol.* 1992, 19, 646. (c) Nicolaou, K. C.; Dai, W. M.; Guy, R. K. *Angew. Chem. Int. Ed. Eng.* 1994, 33, 15. (d) Kingston, D. G. I. *Pharmacol. Ther.* 1991, 52, 1.

2. Schiff, P. B.; Fant, J.; Horwitz, S. B. *Nature,* 1979, 277, 665.

3. Rowinsky, E. K.; Cazenave, L. A.; Donehower, R. C. J. Nat. Cancer Inst. 1990, 82, 1247.
4. McGuire, W. P.; Rowinsky, E. K.; Rosenshein, N. B.; Grumbine, F. C.; Ettinger, D. S.; Armstrong, D. K.; Donehower, R. C. Ann. Int. Med. 1989, 11, 273.
5. Forastiere, A. A., Semin. Oncol. Suppl. 3. 1993, 20, 56.
6. (a) Holton, R. A.; Somoza, C.; Kim, H. B.; Liang, F.; Biediger, R. J.; Boatman, P. D.; Shindo, M.; Smith, C. C.; Kim, S.; Nadizadeh, H.; Suzuki, Y.; Tao, C.; Vu, P.; Tang, S.; Zhang, P.; Murthi, K. M.; Gentile, L. N.; Liu, J. H. J. Am. Chem. Soc. 1994, 116, 1597. (b) Holton, R. A.; Kim, H. B.; Somoza, C.; Liang, F.; Biediger, R. J.; Boatman, P. D.; Shindo, M.; Smith, C. C.; Kim, S.; Nadizadeh, H.; Suzuki, Y.; Tao, C.; Vu, P.; Tang, S.; Zhang, P.; Murthi, K. M.; Gentile, L. N.; Liu, J. H. ibid. 1994, 116, 1599. (c) Nicolaou, K. C.; Nantermet, P. G.; Ueno, H.; Guy, R. K.; Couladouros, E. A.; Sorensen, E. J. ibid. 1995, 117, 624.
7. (a) Ojlma, I.; Habus, I.; Zhao, M.; Zucco, M.; Park, Y. H.; Sun, C. M.; Brigaud, T. Tetrahedron 1992, 48, 6985. (b) Georg, G. I.; Cheruvallath, Z. S.; Himes, R. H.; Mejillano, M R.; Burke, C. T. J. Med. Chem. 1992, 35, 4230. (c) Kingston, D. G. I.; Chaudhary, A. G.; Gunatilaka, A. A. L.; Middleton, M. L. Tetrahedron Lett. 1994, 35, 4483. Baccatin III and 10-deacetylbaccatin III are more abundant than taxol and are found in the needles of several Taxus species. Reconstitution of taxol requires attachment of the phenylisoserine side chain which itself can be synthesized chemically: (d) Bunnage, M. E.; Davies, S. G.; Goodwin, C. J. J. Chem. Soc., Perkin Trans. 1 1994, 77, 2385. (e) Dondoni, A.; Perrone, D.; Semola, T. Synthesis—Stuttgart 1995, 2, 181.
8. (a) Kingston, D. G. I.; Samaranayake, G.; Ivey, C. A. J. Nat. Prod. 1990, 53, 1. (b) Potier, P. Chem. Soc. Rev. 1992, 113. (c) Guenard, D.; Gueritte-Voegelein, F.; Potier, P. Acc. Chem. Res. 1993, 23, 160.
9. (a) Nicolaou, K. C.; Riemer, C.; Kerr, M. A.; Rideout, D.; Wrasidlo, W. Nature 1993, 364, 464. (b) Deutsch, H. M.; Glinski, J. A.; Hernandez, M.; Haugwitz, R. D.; Narayanan, V. L.; Suffness, M.; Zalkow, L. H. . J. Med. Chem. 1989, 32, 788. (c) Mathew, A. E.; Mejillano, M R.; Nath, J. P.; Himes, R. H.; Stella, V. J. J. Med. Chem. 1992, 35, 145. (d) Ueda, Y.; Wong, H.; Matiskella, J. D.; Mikkilineni, A. B.; Farina, V.; Fairchild, C.; Rose, W. C.; Mamber, S. W.; Long, B. H.; Kems, E. H.; Casazza, A. M.; Vyas, D. M. Bioorg. Med. Chem. Lett. 1994, 4, 1861. (e) Zhou, Z.; Kingston, D. G. I.; Crosswell, A. R. J. Natl. Prod. 1991, 54, 1607. (f) Mamber, S. W.; Mikkilineni, A. B.; Pack, E. J.; Rosser, M. P.; Wong, H.; Ueda, Y.; Forenza, S. J. Pharm. Exptl. Therap. 1995, 274, 877. (g) Greenwald, R. B.; Pendri, A.; Bolikal, D.; Gilbert, C. W. Bioorg. Med. Chem. Lett. 1994, 4, 2465. (h) Nicolaou, K. C.; Guy, R. K.; Pitsinos, E. N.; Wrasidlo, W. Angew. Chem. Int. Ed. Eng. 1994, 33, 1583. (i) Greenwald, R. B.; Pendri, A.; Bolikal, D. J. Org. Chem. 1995, 60, 331. (j) Ueda, Y.; Matiskella, J. D.; NEkkilineni, A. B.; Farina, V.; Knipe, J. O.; Rose, W. C.; Casazza, A. M.; Vyas, D. M. Bioorg. Med. Chem. Lett 1995, 5, 247. (k) Greenwald, R. B.; Gilbert, C. W.; Pendri, A.; Conover, C. D.; Xia, J.; Martinez, A. J. Med. Chem 1996, 39, 424.
10. Recently, two enzymes from Nocardioides strains (isolated from soil) were shown to catalyze the regioselective hydrolysis of the 10-acetyl and 13-side chain esters. Since these enzymatic reactions were carried cut in aqueous solutions, they resulted in low productivities (due to the insolubility of taxol) and hydrolytic (and hence degradative) reactions. Hanson, R. L.; Wasylyk, J. M.; Nanduri, V. B.; Cazzulino, D. L.; Patel, R. N.; Szarka, L. J. J. Biol. Chem. 1994, 269, 22145.
11. For reviews on enzymatic catalysis in organic solvents see: (a) Dordick, J. S. in Applied Biocatalysis; Blanch, H. W.; Clark, D. S. Eds.; Marcel Dekker: New York, 1991, Vol. 1, pp. 1–5 1. (b) Klibanov, A. M. Acc. Chem. Res. 1990, 23, 114. (c) Khmelnitsky, Yu. L.; Levashov, A. V.; Klyachko, N. L.; Martinek, K. Enzyme Microb. Technol. 1988, 10, 710. (d) Kvittingen, L. Tetrahedron 1994, 50, 8253.
12. Over 50 different conunercially available lipases and proteases were screened for taxol acylation using vinyl butyrate as the acyl donor. Organic solvents tested included methylene chloride, chloroform, toluene, acetonitrile, vinyl butyrate, diisopropyl ether, 2-pentanone, tetrahydrofuran, dioxane, tert-amyl alcohol, pyridine, and a hexane:tetrahydrofuran mixture (7:3). Reactions were run at 35° C. under shaking for 48 hours. Reaction products were analyzed by HPLC.[14] The following enzymes were found to possess taxol acylation activity: α-chymotrypsin, subtilisin Carlsberg, and thermolysin. Among these enzymes thermolysin showed the highest activity (ca. 3- and 40-fold higher than α-chymotrypsin and subtilisin, respectively) and, therefore, was used as a catalyst in all subsequent reactions.
13. The ability of thermolysin 0 catalyze a transesterification reaction, such as that used in taxol acylation, has never been observed before. This unusual finding reveals an interesting new feature of the zinc-containing protease which has been used as a catalyst for synthesis of peptides: (a) Miyanaga, M.; Tanaka, T.; Sakiyama, T.; Nakanishi, K. Biotechnol. Bioeng. 1995, 46, 631. (b) Persichetti, R. A.; StClair, N. L.; Griffith, J. P.; Navia, M. A.; Margolin, A. L. J. Am. Chem. Soc. 1995, 117, 2732.
14. TLC separations were performed on silica plates (Whatman) using a chloroform/acetonitrile mixture (4:1) as the eluent. In the case of preparative TLC product spots were visualized on the plate under UV irradiation and scraped off the plate. The silica was then extracted with chloroform:acetonitrile (4:1) and the product was isolated by evaporating the solvent under vacuum. $C_{18}$-Reversed-phase HPLC analyses were performed using a linear gradient of a water:acetonitrile (8:3) and isopropanol at 1 ml/min. The HPLC gradient program was as follows (concentrations are given for isopropanol): 0–8 min isocratic at 28%, 8–16 min increasing to 50%, 16–24 min further increasing to 72%, and 24–26 min finally increasing to 100%. Preparative HPLC separations were perfonned using the same gradient program at 7 ml/min.
15. Salt-activated thennolysin was prepared following the published procedure (Khmelnitsky, Yu. L.; Welch, S. H.; Clark, D. S.; Dordick, J. S. J. Am. Chem. Soc. 1994, 116, 2647). To that end, 1 mg/ml of thermolysin was dissolved in 1.6 nm potassium phosphate buffer containing the appropriate amount of KCl. The solution was adjusted to pH 7.5 and lyophilized. The final enzyme preparation contained 5% protein, 1% buffer salt, and 94% KCl.
16. The workup of the reaction mixture included removal of the suspended enzyme by centrifugation and evaporation of the solvent under vacuum.
17. Thermolysin was also capable of catalyzing the regioselective synthesis of taxol carbonates. Specifically, butyl vinyl carbonates[19] was an excellent carbonate donor for saltactivated thermolysin. The reaction was performed in tert-amyl alcohol containing 5 mM taxol, 75 mM butyl vinyl carbonate, and the salt-activated enzyme preparation (5 mg/ml protein.). After 48 h of reaction at 45° C., essentially all of the taxol was converted to two products, taxol 2'-butyl carbonate (15, major) and 7-epitaxol 2'-butyl carbonate (22, minor) (Table 1). Thus, as was the case with taxol ester synthesis, thermolysin-catalyzed taxol carbonate synthesis was specific for the 2'-hydroxyl moiety. In addition to butyl vinyl carbonate, a number of divinyl dicarbonates and acetone oxime vinyl carbonate were used as carbonate donors. In all cases, conversions or taxol ranged from 30 to 100% (Table 1).

18. To verify their potential as prodrugs, two taxol esters, taxol 2'-chloroacetate (2) and taxol 2'-acrylate (3), were tested for cytotoxicity against HL-60 cells, a promyelocytic leukemia cell line, and MOLT-4 cells, a lymphoblastic leukemia cell line.[20] Both derivatives had $IC_{50}$ values about ten times higher than that of taxol for each cell line.

19. Vinyl carbonates were synthesized from vinyl chloroformate and the corresponding alcohols using procedures similar to those published previously: (a) Pozo, M.; Pulido, R.; Gotor, V. *Tetrahedron* 1992, 48, 6477. (b) Matzner, M.; Kurkjy, R. P.; Cotter, R. J. *Chem. Rev.*, 1964, 64, 645.

20. Cells were seeded in 96-well plates at densities of 30,000 cells/well and grown in RPMI-1640 medium containing 10% bovine calf serum at 37° C. for 24 h. The medium was then replaced with fresh medium containing the taxol esters (excluding taxol, which had been removed by preparative TLC) dissolved in DMSO at final concentrations ranging from 100 nM to 0.1 nM. The final concentration of DMSO in the cell medium was 0.5%. After 72 h, samples were removed for cell counts. Total cell number and viability were determined by trypan blue exclusion and manual cell counting on a hemacytometer.

21. A great deal of evidence exists that lipases are highly selective for the primary hydroxyl of monosaccharides in transesterification reactions: (a) Martin, B. D.; Ampofo, S. A.; Linhardt, R. J.; Dordick, J. S. *Macromolecules*, 1992, 25, 7081. (b) Therisod, M.; Klibanov, A. M. *J. Am. Chem. Soc.* 1986, 108, 5638. (c) Ljunger, G.; Adlercreutz, P.; Mattiasson, V. *Biotechnol. Lett.* 1994, 16, 1167.

22. Although the chemical acylation of taxol at the 2' position is facile[96], the subsequent modification of such an ester group may be complicated by the presence of native esters on the taxol nucleus which may be labile to non-selective hydrolysis/transesterification. This is in stark contrast to the high regioselectivity of enzymatic catalysis as demonstrated in this work.

23. (a) Mellado, W.; Magri, N. F.; Kingston, D. G. I.; Garcia-Arenas, R.; Orr, G. A.; Horwitz, S. B. *Biochem. Biophys. Res. Commun.* 1984, 124, 329. (b) Magri, N. F.; Kingston, D. G. I. *J. Nat. Prod.* 1988, 51, 298.

24. Ringel, I.; Horwitz, S. B. *J. Pharmac. Exp. Ther.* 1987, 242, 692.

25. (a) Huang, C. H. O.; Kingston, D. G. I.; Magri, N. F.; Samaranayake, G.; Boettner, F. E. *J. Nat. Prod.* 1986, 49, 665. (b) Chmurny, G. N.; Hilton, B. D.; Brobst, S.; Look, S. A.; Witherup, K. M.; Beurler, J. A. *J. Nat. Prod.* 1992, 55, 414.

What is claimed as new and is desired to be secured by Letters Patent of the United States is:

1. A taxol derivative of the formula:

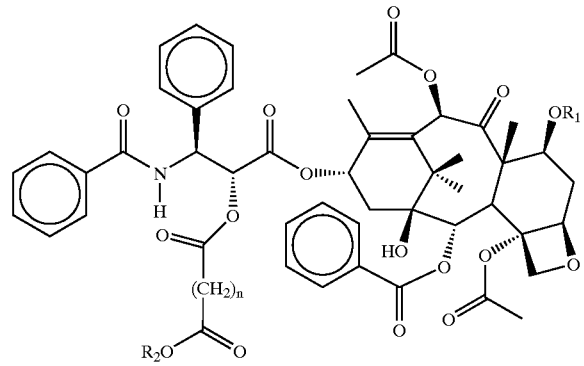

wherein:

$R_1$ is hydrogen, $C_{1-10}$ alkyl ester, halosubstituted $C_{1-10}$ alkyl ester, or $CO(CH_2)_x COR_3$ where x is an integer of 2–10 and $R_3$ is hydrogen, $C_{1-10}$ alkyl or $C_{1-10}$ alkenyl; n is an integer of 5–10; and $R_2$ is hydrogen, $C_{1-10}$ alkyl, $C_{1-10}$ alkenyl, or a 6 substituted saccharide compound selected from the group consisting of glucose, galactose, allose, altrose, mannose, gulose, idose, talose, lactose, cellobiose, sucrose, fructose, deoxynojirimycin, N-acetyl glucosamine, N-acetyl galactosamine, and maltose.

2. The taxol derivative according to claim 1, wherein n is 4.

3. The taxol derivative according to claim 1, wherein n is 5.

4. The taxol derivative according to claim 1, wherein n is 6.

5. The taxol derivative according to claim 1, wherein n is 7.

6. The taxol derivative according to claim 1, wherein n is 8.

7. The taxol derivative according to claim 1, wherein n is 9.

8. The taxol derivative according to claim 1, wherein n is 10.

9. The taxol derivative according to claim 1, wherein $R_1$ is hydrogen.

10. The taxol derivative according to claim 1, wherein $R_1$ is $C_{1-10}$ alkyl ester.

11. The taxol derivative according to claim 1, wherein $R_1$ is halosubstituted $C_{1-10}$ alkyl ester.

12. The taxol derivative according to claim 1, wherein $R_1$ is $CO(CH_2)_x COR_3$, where x is an integer of 2–10 and $R_3$ is hydrogen.

13. The taxol derivative according to claim 1, wherein $R_1$ is $C_{1-10}$ alkyl.

14. The taxol derivative according to claim 1, wherein $R_1$ is $C_{1-10}$ alkenyl.

15. The taxol derivative according to claim 1, wherein $R_2$ is hydrogen.

16. The taxol derivative according to claim 1, wherein $R_2$ is a $C_{1-10}$ alkyl.

17. The taxol derivative according to claim 1, wherein $R_2$ is a $C_{1-10}$ alkenyl.

18. The taxol derivative according to claim 1, wherein $R_2$ is a 6 substituted saccharide compound.

* * * * *